US006291511B1

(12) United States Patent
Durette et al.

(10) Patent No.: US 6,291,511 B1
(45) Date of Patent: Sep. 18, 2001

(54) BIARYLALKANOIC ACIDS AS CELL ADHESION INHIBITORS

(75) Inventors: Philippe L. Durette, New Providence; William K. Hagmann, Westfield; Malcolm MacCoss, Freehold; Sander G. Mills, Scotch Plains; Richard A. Mumford, Red Bank, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/359,015

(22) Filed: Jul. 22, 1999

Related U.S. Application Data

(63) Continuation of application No. 09/085,793, filed on May 28, 1998, now abandoned.
(60) Provisional application No. 60/047,856, filed on May 29, 1997, and provisional application No. 60/066,831, filed on Nov. 25, 1997.

(51) Int. Cl.⁷ .......................... C07D 207/08; A61K 31/40
(52) U.S. Cl. ........................ 514/423; 548/537; 514/422
(58) Field of Search .................................... 548/543, 537; 514/424, 423, 422

(56) References Cited

U.S. PATENT DOCUMENTS

| 5,506,244 | 4/1996 | Fink . |
| 5,510,332 | 4/1996 | Kogan et al. . |
| 5,763,604 | 6/1998 | Ackermann et al. . |

FOREIGN PATENT DOCUMENTS

| WO 95/12611 | 5/1995 | (WO) . |
| WO 95/15973 | 6/1995 | (WO) . |
| WO 96/01644 | 1/1996 | (WO) . |
| WO 96/06108 | 2/1996 | (WO) . |
| WO 96/20216 | 7/1996 | (WO) . |
| WO 96/22966 | 8/1996 | (WO) . |
| WO 96/31206 | 10/1996 | (WO) . |
| WO 94/40641 PCT | 12/1996 | (WO) . |
| WO 96/40781 | 12/1996 | (WO) . |
| WO 97/02289 | 1/1997 | (WO) . |
| WO 97/03094 | 1/1997 | (WO) . |
| WO 98/53814 PCT | 12/1998 | (WO) . |
| WO 98/53818 PCT | 12/1998 | (WO) . |
| WO 99/06431 | 2/1999 | (WO) . |

OTHER PUBLICATIONS

Bio Organic & Medical Chemistry Letters, vol. 6, No. 21, pp. 24–2500, 1996.

J. Med. Chem. 1997, 40, 3359–3368.

Guenoun, et al., Tetrahedron Letters, vol. 31(15), pp. 2153–2156, 1990.

*Primary Examiner*—Zinna Northington Davis
(74) *Attorney, Agent, or Firm*—Mollie M. Yang; David L. Rose

(57) ABSTRACT

Compounds of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

11 Claims, No Drawings

BIARYLALKANOIC ACIDS AS CELL ADHESION INHIBITORS

This application is a continuation of application Ser. No. 09/085,793 filed on May 28, 1998, now abandoned which is based on, and claims pliority from provisional applications Ser. No. 60/047,856 filed 29 May 1997 and Ser. No. 60/066,831 filed Nov. 25, 1997. The or applications are hereby incorporated by reference in their entirety.

SUMMARY OF THE INVENTION

The compounds of the present invention are antagonists of the VLA-4 integrin ("very late antigen-4"; CD49d/CD29; or $\alpha_4\beta_1$) and/or the $\alpha_4\beta_7$ integrin (LPAM-1 and $\alpha_4\beta_p$), thereby blocking the binding of VLA-4 to its various ligands, such as VCAM-1 and regions of fibronectin and/or $\alpha_4\beta_7$ to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4 and/or $\alpha_4\beta_7$ binding and cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, and atherosclerosis.

BACKGROUND OF THE INVENTION

The present invention relates to biaryalkanoic acid derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, *Cell*, 67, 1033 (1991); T. A. Springer, *Cell*, 76, 301 (1994); D. Cox et al., "The Pharmacology of the Integrins." *Medicinal Research Rev.* 14, 195 (1994) and V. W. Engleman et al., "Cell Adhesion Integrins as Pharmaceutical Targets." in *Ann. Repts. in Medicinal Chemistry*, Vol. 31, J. A. Bristol, Ed.; Acad. Press, NY, 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of of these cell types (see M. E. Hemler, "VLA Proteins in the Integrin Family: Structures, Functions, and Their Role on Leukocytes." *Ann. Rev. Immunol.* 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to proinflammatory cytokines (See A. J. H. Gearing and W. Newman, "Circulating adhesion molecules in disease.", *Immunol. Today*, 14, 506 (1993). The CS-1 domain is a 25 amino acid sequence that arises by alternative splicing within a region of fibronectin. (For a review, see R. O. Hynes "Fibronectins.", Springer-Velag, NY, 1990.) A role for VLA-4/CS-1 interactions in inflammatory conditions has been proposed (see M. J. Elices, "The integrin $\alpha_{41}$ (VLA-4) as a therapeutic target" in *Cell Adhesion and Human Disease*, Ciba Found. Symp., John Wiley & Sons, NY, 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract (see C. M. Parker et al., *Proc. Natl. Acad. Sci. USA*, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., *Nature*, 363, 461 (1993); A. Hamann et al., *J. Immunol.*, 152,3282 (1994)). MadCAM-1 can be induced in vitro by proinflammatory stimuli (See E. E. Sikorski et al. *J. Immunol.*, 151, 5239 (1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." *Nature*, 356, 63 (1993) and E. Keszthelyi et al., "Evidence for a prolonged role of $\alpha_4$ integrin throughout active experimental allergic encephalomyelitis." *Neurology*, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." *J. Clin.*

*Invest.* 93, 776 (1993) and A. A. Y. Milne and P. P. Piper, "Role of VLA-4 integrin in leucocyte recruitment and bronchial hyperresponsiveness in the gunea-pig." *Eur. J. Pharmacol.*, 282, 243 (1995)); iii) adjuvant-induced arthritis in rats as a model of inflammatory arthritis (see C. Barbadillo et al., "Anti-VLA-4 mAb prevents adjuvant arthritis in Lewis rats." *Arthr. Rheuma.* (Suppl.), 36 95 (1993) and D. Seiffge, "Protective effects of monoclonal antibody to VLA-4 on leukocyte adhesion and course of disease in adjuvant arthritis in rats." *J. Rheumatol.*, 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", *J. Clin. Invest.*, 93, 1700 (1994), A. Jakubowski et al., "Vascular cell adhesion molecule-Ig fusion protein selectively targets activated $\alpha_4$-integrin receptors in vivo: Inhibition of autoimmune diabetes in an adoptive transfer model in nonobese diabetic mice." *J. Immunol.*, 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", *Tranplant. Proc.*, 26, 867 (1994) and S. Molossi et al., "Blockade of very late antigen-4 integrin binding to fibronectin with connecting segment-i peptide reduces accelerated coronary arteripathy in rabbit cardiac allografts." *J. Clin Invest.*, 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin $\alpha$-4 subunit inhibit the murine contact hypersensitivity response." *Eur. J. Immunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91,577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of $\alpha$4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996; xii) inhibition of TH2 T-cell cytokine production including IL-4 and IL-5 by VLA-4 antibodies which would attenuate allergic responses (J.Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; acute respiratory distress syndrome (ARDS); atherosclerotic plaque formation; restenosis; uveitis and circulatory shock (for examples, see A. A. Postigo et al., "The $\alpha_4\beta_1$/VCAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89,375 (1996)).

At present, there is a humanized monoclonal antibody (Antegren® Athena Neurosciences/Elan ) against VLA-4 in clinical development for the treatment of "flares" associated with multiple sclerosis and a humanized monoclonal antibody (ACT-1®/LDP-02 LeukoSite) against $\alpha_4\beta_7$ in clinical development for the treatment of inflammatory bowel disease. Several peptidyl antagonists of VLA-4 have been described (D. Y. Jackson et al., "Potent $\alpha_4\beta_1$ peptide antagonists as potential anti-inflammatory agents", *J. Med. Chem.*, 40, 3359 (1997); H. N. Shroff et al., "Small peptide inhibitors of $\alpha_4\beta_7$ mediated MadCAM-1 adhesion to lymphocytes", *Bioorg. Med. Chem. Lett.*, 6, 2495 (1996); U.S. Pat. No. 5,510,332, WO97/03094, WO97/02289, WO96/40781, WO96/22966, WO96/20216, WO96/01644, WO96/06108, WO95/15973). There is one report of non-peptidyl inhibitors of the ligands for $\alpha_4$-integrins (WO96/31206). There still remains a need for low molecular weight, specific inhibitors of VLA-4- and $\alpha_4\beta_7$-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and $\alpha_4\beta_7$ binding and cell adhesion and activation.

DETAILED DESCRIPTION OF THE INVENTION

The present invention provides novel compounds of Formula I

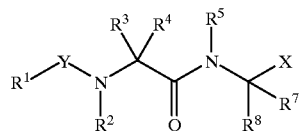

or a pharmaceutically acceptable salt thereof wherein:
$R^1$ is
1) $C_{1-10}$alkyl,
2) $C_{2-10}$alkenyl,
3) $C_{2-10}$alkynyl,
4) Cy,
5) Cy-$C_{1-10}$alkyl, 6) Cy-$C_{2-10}$alkenyl,
7) Cy-$C_{2-10}$alkynyl,
wherein alkyl, alkenyl, and alkynyl are optionally substituted with one to four substituents independently selected from $R^a$; and Cy is optionally substituted with one to four substituents independently selected from $R^b$;

$R^2$ and $R^3$ are independently
1) hydrogen, or
2) a group selected from $R^1$; or $R^2$ and $R^3$ together with the atoms to which they are attached form a ring of 4 to 7 members containing 0–2 additional heteroatoms independently selected from oxygen, sulfur and nitrogen, wherein said ring may be isolated or benzo-fused, and optionally substituted with one to four substituents independently selected from $R^b$;

$R^4$ and $R^7$ are independently selected from the group consisting of
1) hydrogen,
2) $C_{1-10}$alkyl,
3) $C_{2-10}$alkenyl,
4) $C_{2-10}$alkynyl,
5) aryl,
6) aryl $C_{1-10}$alkyl,
7) heteroaryl, and
8) heteroaryl $C_{1-10}$alkyl,
wherein alkyl, alkenyl and alkynyl are optionally substituted with one to four substituents independently selected from $R^a$, and aryl and heteroaryl are optionally substituted with one to four substituents independently selected from $R^b$; or R3, R4 and the carbon to which they are attached form a 3–7 membered ring optionally containing 0–2 heteroatoms selected from N, O and S;

$R^5$ is
1) hydrogen,
2) $C_{1-10}$alkyl optionally substituted with one to four substituents independently selected from $R^a$, or
3) Cy optionally substituted with one to four substituents independently selected from $R^b$, $R^6$ is
1) $Ar^1$–$Ar^2$–$C_{1-10}$alkyl,
2) $Ar^1$–$Ar^2$–$C_{2-10}$alkenyl,
3) $Ar^1$–$Ar^2$–$C_{2-10}$alkynyl,
wherein $Ar^1$ and $Ar^2$ are independently aryl or heteroaryl each of which is optionally substituted with one to four substituents independently selected from $R^b$; alkyl, alkenyl and alkynyl are optionally substituted with one to four substituents independently selected from $R^a$;

$R^a$ is
1) Cy
2) —$OR^d$,
3) —$NO_2$,
4) halogen
5) —$S(O)_m R^d$,
6) —$SR^d$,
7) —$S(O)_2 OR^d$,
8) —$S(O)_m NR^d R^e$,
9) —$NR^d R^e$,
10) —$O(CR^f R^g)_n NR^d R^e$,
11) —$C(O)R^d$,
12) —$CO_2 R^d$,
13) —$CO_2(CR^f R^g)_n CONR^d R^e$,
14) —$OC(O)R^d$,
15) —CN,
16) —$C(O)NR^d R^e$,
17) —$NR^d C(O)R^e$,
18) —$OC(O)NR^d R^e$,
19) —$NR^d C(O)OR^e$,
20) —$NR^d C(O)NR^d R^e$,
21) —$CR^d(N$—$OR^e)$,
22) $CF_3$; or
23) —$OCF_3$;
wherein Cy is optionally subsituted with one to four substituents independently selected from $R^c$;

$R^b$ is
1) a group selected from $R^a$,
2) $C_{1-10}$alkyl,
3) $C_{2-10}$alkenyl,
4) $C_{2-10}$alkynyl,
5) aryl $C_{1-10}$alkyl,
6) heteroaryl $C_{1-10}$alkyl,
wherein alkyl, alkenyl, alkynyl, aryl, heteroaryl are optionally substituted with a group independently selected from $R^c$;

$R^c$ is
1) halogen,
2) amino,
3) carboxy,
4) $C_{1-4}$alkyl,
5) $C_{1-4}$alkoxy,
6) aryl,
7) aryl $C_{1-4}$alkyl,
8) hydroxy,
9) $CF_3$, or
8) aryloxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy–$C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is
1) hydrogen,
2) $C_{1-10}$alkyl,
3) $C_{1-10}$alkenyl,
4) $C_{1-10}$alkynyl,
5) cyano,
6) aryl,
7) aryl $C_{1-10}$alkyl,
8) heteroaryl,
9) heteroaryl $C_{1-10}$alkyl, or
10) —$SO_2 R^i$;
wherein alkyl, alkenyl, and alkynyl are optionally substituted with one to four substituents independently selected from $R^a$; and aryl and heteroaryl are each optionally substituted with one to four substituents independently selected from $R^b$;

$R^i$
1) $C_{1-10}$alkyl,
2) $C_{2-10}$alkenyl,

3) $C_{2-10}$alkynyl, or 4) aryl;

wherein alkyl, alkenyl, alkynyl and aryl are each optionally substituted with one to four substituents independently selected from $R^c$;

Cy is cycloalkyl, heterocyclyl, aryl, or heteroaryl;

m is an integer from 1 to 2;

n is an integer from 1 to 10;

X is
1) —C(O)OR$^d$,
2) —P(O)(OR$^d$)(OR$^e$)
3) —P(O)(R$^d$)(OR$^e$)
4) —S(O)$_m$OR$^d$,
5) —C(O)NR$^d$R$^h$, or
6) —5-tetrazolyl;

Y is
1) —C(O)—,
2) —O—C(O)—,
3) —NR$^e$—C(O)—,
4) —S(O)$_2$—,
5) —P(O)(OR$^i$)
6) C(O)C(O).

In one embodiment, $R^1$ is $C_{1-10}$alkyl, aryl, aryl-$C_{1-10}$alkyl, heteroaryl or heteroaryl-$C_{1-10}$alkyl, wherein alkyl, aryl and heteroaryl are optionally substituted as provided for under formula I. In a preferred embodiment $R^1$ is phenyl optionally substituted with one to three groups selected from $R^b$.

In another embodiment, $R^2$ is hydrogen, $C_{1-10}$alkyl, Cy or Cy—$C_{1-10}$alkyl; or $R^2$, $R^3$ together with the atoms to which they are attached form a ring of 4 to 7 members containing 0–2 additional heteroatoms independently selected from oxygen, sulfur and nitrogen, wherein said ring may be isolated or benzo-fused, and optionally substituted with one to four substituents independently selected from $R^b$. Preferably R2, R3 together with the atoms to which they are attached form a ring of 5 to 6 members containing 0–2 additional heteroatoms independently selected from oxygen, sulfur and nitrogen, wherein said ring may be isolated or benzo-fused, and optionally substituted with one to four substituents independently selected from $R^b$.

In another embodiment $R^4$ is H, $C_{1-10}$alkyl, aryl, heteroaryl, aryl-$C_{1-10}$alkyl or heteroaryl-$C_{1-10}$alkyl. Preferably, $R^4$ is H or $C_{1-10}$alkyl.

In another embodiment $R^6$ is Ar$^1$–Ar$^2$–$C_{1-10}$alkyl wherein Ar1 and Ar2 are optionally substituted with from 1 to 4 groups independently selected from $R^b$. Preferably $R^6$ is Ar$^1$–Ar$^2$–$C_{1-3}$alkyl wherein Ar1 and Ar2 are optionally substituted with from 1 to 4 groups independently selected from $R^b$.

In another embodiment X is C(O)OR$^d$.

In yet another embodiment Y is C(O) or S(O)$_2$.

In a preferred embodiment of compounds of Formula I are compounds of formula Ia:

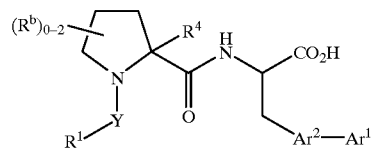

Ia wherein
$R^1$ is
1) $C_{1-10}$alkyl,
2) Cy, or
3) Cy—$C_{1-10}$alkyl,
wherein alkyl is optionally substituted with one to four substituents independently selected from $R^a$; and Cy is optionally substituted with one to four substituents independently selected from $R^b$;

$R^4$ is
1) hydrogen, or
2) $C_{1-3}$alkyl;

Ar$^1$ and Ar$^2$ are independently aryl or heteroaryl each of which is optionally substituted with one to four substituents independently selected from $R^b$;

Y is C(O) or SO$_2$; and $R^b$ is as defined under formula I.

In one subset of formula Ia are compounds wherein R1 is Cy optionally substituted with one to three groups independently selected from $R^b$. For the purpose of R1 Cy is preferably aryl or heteroaryl optionally substituted with one to four substituents selected from $R^b$. More preferred $R^1$ is phenyl with a substituent on the 3-position and optionally a second substituent; the more preferred substituents are selected from $C_{1-10}$alkoxy, halogen, cyano, and trifluoromethyl.

In another subset of formula Ia are compounds wherein Ar$^2$ is phenylene.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclopentyl, cyclohexyl, cycloheptyl, etrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha_4\beta_7$ integrin makes them useful for preventing or reversing the symptoms, disorders or diseases induced by the binding of VLA-4 and or $\alpha_4\beta_7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha_4\beta_7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, and (19) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
| --- | --- |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\beta$2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone, pioglitazone, englitazone, MCC-555, BRL49653 and the like); (1) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying schemes. In the first method (Scheme 1), a resin-based synthetic strategy is outlined where the resin employed is represented by the ball (●). An N-Fmoc-protected amino acid derivative A (Fmoc=fluorenylmethoxycarbonyl) is loaded on to the appropriate hydroxyl-containing resin using dicyclohexylcarbodiimide (DCC) and 1-hydroxybenzotriazole (HOBt) in dimethylformamide (DMF) to give R The Fmoc protecting group is removed with piperidine in DMF to yield free amine C. The next Fmoc-protected amino acid derivative D is coupled to C employing standard peptide (in this instance, 2-(1H-benzotriazol-1-yl)-1,1,3,3-tetramethyluronium hexafluorophosphate (HBTU), HOBt, and N,N-diisopropylethylamine (DIEA) in DMF) to yield dipeptide E. The Fmoc group is removed with piperidine in DMF to yield the free amine F. An acid chloride or isocyanate derivative is reacted with F in the presence of DIEA to yield G. The final product is removed from the resin with strong acid (in this instance, trifluoroacetic acid (TFA) in the presence of thioanisole and ethanedithiol) to yield compounds of the present invention H.

In the second method (Scheme 2), standard solution phase synthetic methodology is outlined. An N-Boc-protected amino acid derivative A (Boc=tert-butyloxycarbonyl) is treated with tert-butyl 2,2,2-trichloroacetimidate in the presence of boron trifluoride etherate followed by treatment with strong acid (HCl in ethyl acetate or sulfuric acid in t-butyl acetate) to remove the t-BOC group to yield tert-butyl ester B which is subsequently coupled to Cbz-protected amino acid derivative C (Cbz=carbobenzyloxy) in the presence of 1-(3-dimethylaminopropyl)-3-ethylcarbodiimide hydrochloride (EDC), HOBt, and N-methylmorpholine (NMM) in methylene chloride to yield dipeptide D. Catalytic hydrogenation of D in the presence of a palladium-on-carbon (Pd/C) catalyst yields E. Reaction of E with an acid chloride or isocyanate in the presence of DIEA and 4-dimethylaminopyridine (DMAP) yields F which is subsequently reacted with strong acid (TFA) to yield the desired product G.

Scheme 1

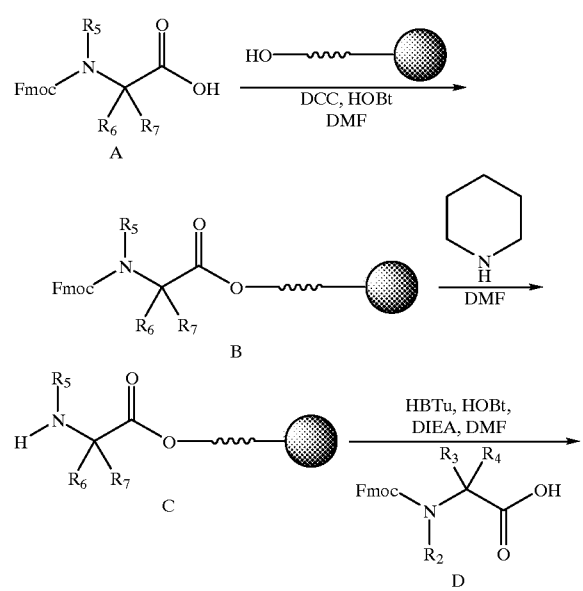

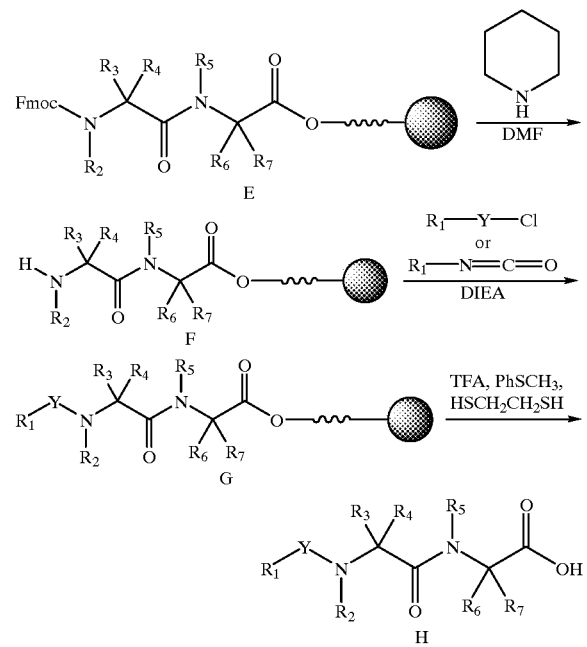

Scheme 2

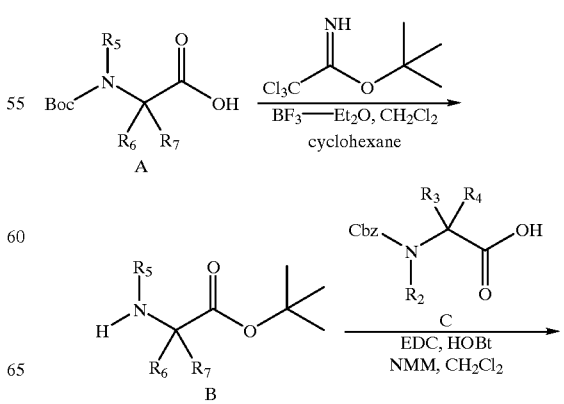

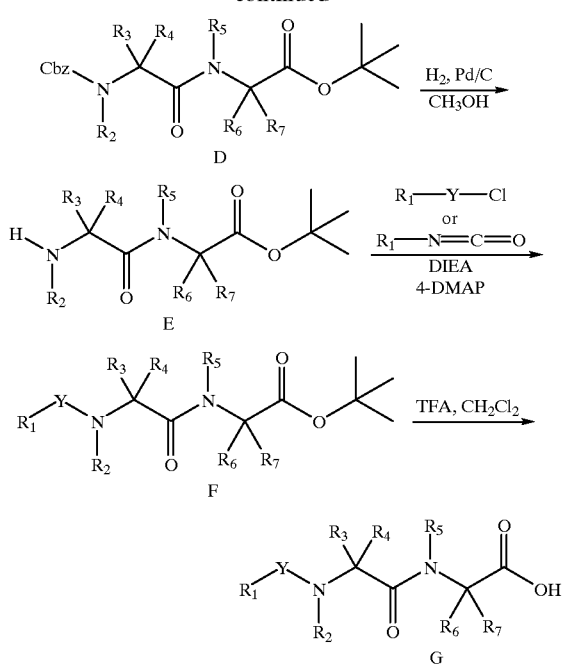

In the third method (Scheme 3), a late stage intermediate aryl bromide or iodide is coupled to an appropriately substituted aryl or heteroaryl boronic acid to give a subset of compounds of the present invention ($R^6$=biaryl-substituted alkyl, $R^7$=hydrogen). For example, amino acid methyl ester A is reacted with an acid chloride or isocyanate in the presence of DIEA to yield R Basic hydrolysis of the methyl ester yields amino acid derivative C. N-Boc-4-iodo- or 4-bromo-phenylalanine D is reacted with tert-butyl 2,2,2-trichloroacetimidate in the presence of boron trifluoride etherate in methylene chloride-cyclohexane followed by treatment with strong acid (HCl in ethyl acetate or sulfuric acid in t-butyl acetate) to remove the t-BOC group to yield tert-butyl ester E which is subsequently coupled with C in the presence of EDC, HOBt and NMM to yield 4-iodo- or 4-bromo-phenylalanine dipeptide F. Substituted aryl or heteroaryl boronic acids are coupled to F in the presence of a palladium(O) reagent, such as tetrakis(triphenylphosphine) palladium under Suzuki conditions (N. Miyaura et al., *Synth. Commun.*, 1981, 11, 513–519) to yield G. The tert-butyl ester is then removed by treatment with strong acid (TFA) to yield the desired product H. If the aryl or heteroaryl boronic acid is not commercially available, but the corresponding bromide or iodide is, then the bromide or iodide can be converted into the desired boronic acid by treatment with an alkyllithium reagent in tetrahydrofuran at low temperature followed by addition of trimethyl or triisopropyl borate. Hydrolysis to the boronic acid can be effected by treatment of the intermediate with aqueous base and then acid.

Scheme 3

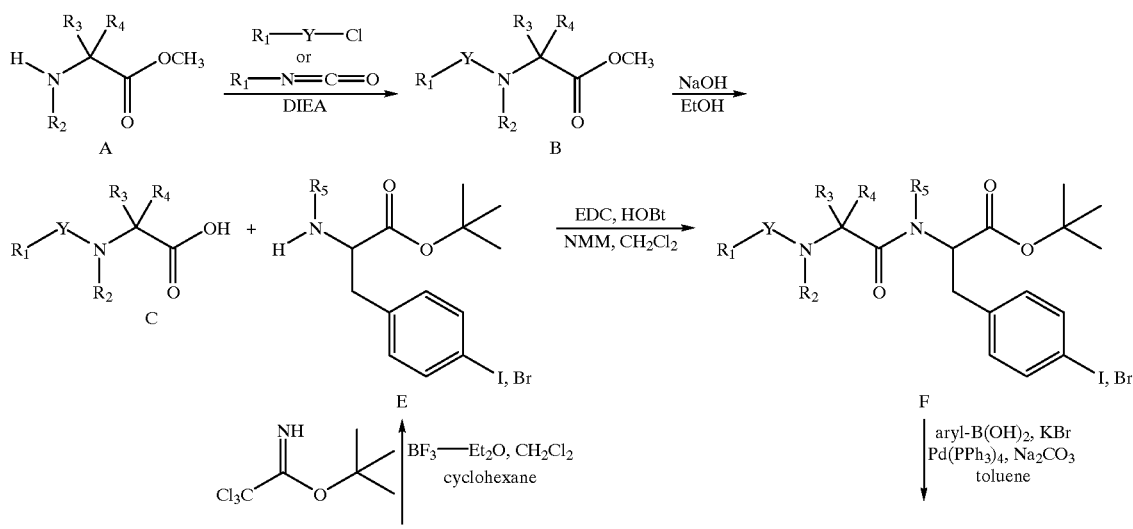

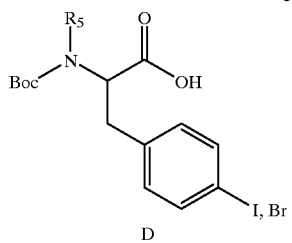

D

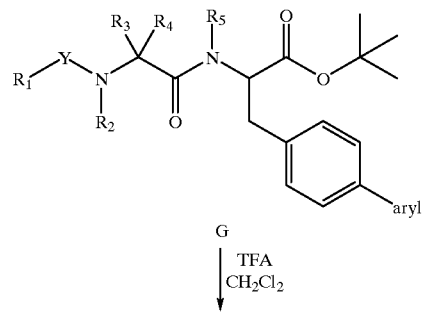

G

TFA
CH$_2$Cl$_2$

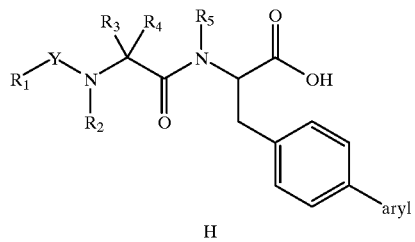

H

Alternatively, the aryl coupling reaction may be performed by application of Stille-type carbon-carbon bond forming conditions (Scheme 4). (A. M. Echavarren and J. K. Stille, *J. Am. Chem. Soc.* 1987, 109, 5478–5486). The aryl bromide or iodide intermediate A is converted into its trialkyltin derivative B using hexamethylditin in the presence of a palladium(0) catalyst and lithium chloride and then reacted with an appropriately substituted aryl or heteroaryl bromide, iodide, or triflate in the presence of a palladium reagent, such as tetrakis(triphenylphosphine)palladium(0) or tris(dibenzylideneacetone)dipalladium(0), in a suitable solvent, such as toluene, dioxane, DMF, or 1-methyl-2-pyrrolidinone, to give intermediate C. The tert-butyl ester is then removed by treatment with strong acid (TFA) to yield the desired product D.

Scheme 4

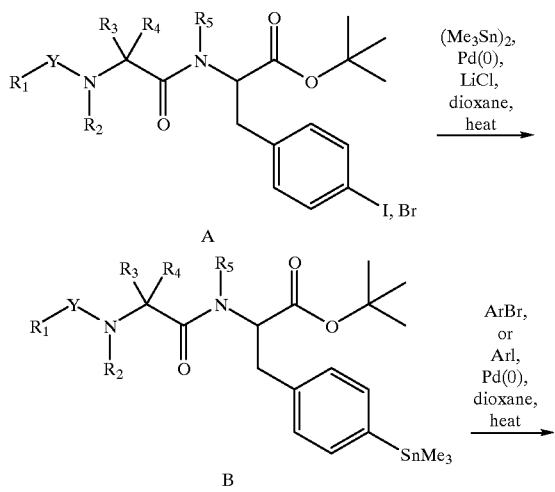

-continued

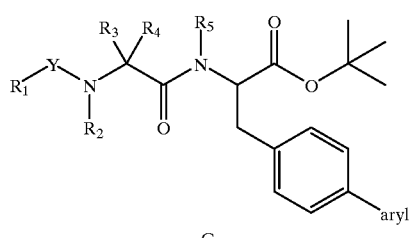

C

TFA
CH$_2$Cl$_2$

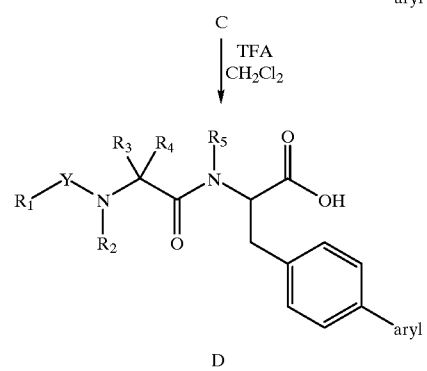

D

Compounds wherein the middle ring is heteroaryl (E) may be prepared (Scheme 5) in a similar fashion starting from the appropriate heteroaryl bromide or iodide C using Suzuki-type conditions as depicted in Scheme 3 or from the corresponding heteroaryl trimethyltin intermediate D using Stille-type conditions as depicted in Scheme 4. The requisite heteroaryl halides C may be prepared via conventional electrophilic halogenation of the N-Boc-heteroaryl-alanine tert-butyl ester intermediate B. B may be prepared from the known aliphatic iodo intermediate A in carbon-carbon bond formation using zinc/copper couple and palladium(II) (M. J. Dunn et al., *SYNLETT* 1993, 499–500).

Scheme 5

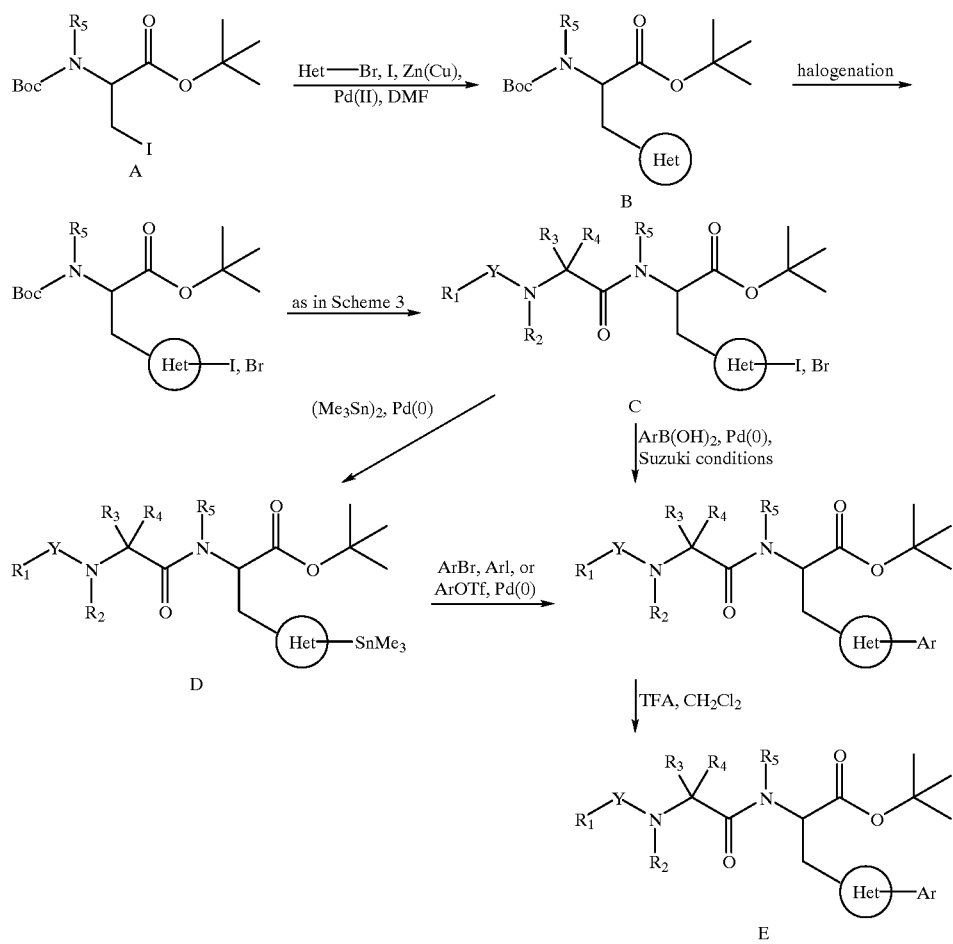

Het = heteraryl;
Ar = aryl or heteroaryl

General Procedure for the Solid-phase Synthesis of Compounds of Formula 1

Step A. Loading of N-Fmoc-amino Acid Derivatives onto Resins.

N-Fmoc-amino acids were loaded on either Wang® (Calbiochem-Novabiochem Corp.) or Chloro (2-chlorotrityl) resin. Wang® resin, typically 0.3 mmol, was washed with dimethylformamide three times. A solution of N-Fmoc-amino acid (0.3 mmol) in dimethylformamide (3 mL) was transferred to the pre-swollen Wang® resin. Dicyclohexylcarbodiimide (0.3 mmol) and 1-N-hydroxybenztriazole (0.3 mmol) was added and the mixture gently swirled for 2 hours. Following filtration, the resin was sequentially washed with dimethylformamide (3 times) and dichloromethane (3 times). The amino acid substitution value obtained after vacuum drying typically ranged between 0.07 to 0.1 mmol.

Alternatively, Chloro (2-chorotrityl) resin, typically 0.2 mmol, was pre-swollen in dimethylformamide. A solution of N-Fmoc-amino acid (0.2 mmol) in dimethylformamide (3 ml) was added to the resin, followed by the addition of N,N-diisopropylethylamine (0.4 mmol). The resin was gently stirred for 2 hours, filtered and washed sequentially with dimethylformamide (3 times) and dichloromethane (3 times). The resin was finally washed with 10% methanol in dichloromethane and vacuum dried. The amino acid substitution value obtained after vacuum drying typically ranged between 0.05 to 0.1 mmol.

Step B. Deprotection of the N-Fmoc Group.

The N-Fmoc protecting group was removed from the resin from Step A by treatment with 20% piperidine in dimethylformamide for minutes. Following filtration, the resin was washed sequentially with dimethylformamide (3 times), dichloromethane (1 time) and dimethylformamide (2 times) and used in the subsequent reaction.

Step C. Coupling of the Next N-Fmoc-amino Acid Derivative

A solution of the next desired N-Fmoc-amino acid derivative (0.4 mmol) in dimethylformamide (2 mL) was mixed with 2-(1H-benzotriazol-1-yl)-1,1,3,3-tetramethyluronium hexafluorophosphate (0.4 mmol), 1-hydroxybenzotriazole (0.4 mmol) and diisopropylethylamine (0.6 mmol). This solution was transferred to resin from Step B and typically allowed to react for 2 hours. Couplings were monitored by ninhydrin reaction. The coupling mixture was filtered and the resin ashed with dimethylformamide (3 times) and used in the subsequent reaction.

Step D. Deprotection of the N-Fmoc Group.

The N-Fmoc protecting group was removed from the resin from Step C by the procedure described in Step B and used in the subsequent reaction. Step E. Acylation (or sulfonylation) of the terminal amino group.

The desired N-terminal capping reagent (sulfonyl chloride or other acyl chloride) (0.4 mol) was dissolved in dimethylformamide (2 ml), mixed with N,N-diisopropylethylamine(0.8 mmol) and added to the resin from Step D. After approximately two hours, the resin was sequentially washed with dimethylformamide (3 times) and dichloromethane (3 times). Step F. Cleavage of the desired products from the resins.

The final desired products were cleaved from the resins from Step E by gently stirring with a solution of trifluoroacetic acid:thioanisole:ethanedithiol (95:2.5:2.5); 3 hours for Wang® resin and minutes for the Chloro (2-chorotrityl) resin. Following filtration, the solvents were removed by evaporation and the residue dissolved in acetonitrile (3 mL). Insoluble material was removed by filtration. The final products were purified by reverse phase chromatography with a linear gradient of buffer A (0.1% trifluoroacetic acid in water) and buffer B (0.1% trifluoroacetic acid in acetonitrile) and isolated by lyophilization. Molecular ions were obtained by electrospray ionization mass spectrometry or matrix-assisted laser desorption ionization time-of-flight mass spectrometry to confirm the structure of each peptide.

The following examples are provided to illustrate the present invention and are not to be construed as limiting its scope in any manner.

The following compounds were prepared by the above general procedures using the appropriate amino acid derivatives and acyl or sulfonyl chloride.

|  | Example | Compound Name | MS* |
|---|---|---|---|
| 1-808085 | (1) | N-(3,4-dimethoxybenzenesulfonyl)-1,2,3,4-tetrahydro-isoquinoline-3(S)-carbonyl-(L)-biphenylalanine | 601 |
|  | (2) | N-(3,5-dichlorobenzenesulfonyl)-(L)-prolyl-(L)-4-biphenylalanine | 548 |

*m/e, M + 1

EXAMPLE 3 (L-817,229)

N-(3,5-Dichlorobenzenesulfonyl)-(L-)-prolyl-(L)-4-(4-fluorophenyl)phenylalanine

Step A: 4-Iodo-(L)-phenylalanine, tert-butyl ester hydrochloride.

To a suspension of N-Boc-4-iodo-(L)-phenylalanine (1.0 g, 2.56 mmol) in methylene chloride (7 mL) and cyclohexane (14 mL) were added t-butyl trichloroacetimidate (0.48 mL, 2.68 mmol) and boron trifluoride-etherate (48 µL). The reaction mixture was stirred for 5 hours at room temperature under a nitrogen atmosphere and then treated a second time with the same amounts of t-butyl trichloroacetimidate and boron trifluoride-etherate as above. After stirring overnight, a third addition was made, and the mixture was stirred a further 3 hours. The mixture was then filtered and the filtrate evaporated. The product was obtained pure by silica gel chromatography eluting with 10% diethyl ether in hexane; yield 650 mg. The product was treated with 1M HCl in ethyl acetate (7.3 mL) for 18 hours at room temperature. The mixture was evaporated and coevaporated several times with diethyl ether to afford the title compound; yield 522 mg.

400 MHz $^1$H NMR (CD$_3$OD): δ 1.42 (s, 9H); 3.13 (d, 2H); 4.18 (t, 1H); 7.09 d, 2H); 7.75 (d, 2H).

Step B: N-(3,5-Dichlorobenzenesulfonyl)-(L)-proline p To a mixture of (L)-proline methyl ester hydrochloride (838 mg, 5.06 mmol) in methylene chloride (25 mL) at 0° C. were added N,N-diisopropylethylamine (2.64 mL, 15.2 mmol) and a solution of 3,5-dichlorobenzenesulfonyl chloride (1.49 g, 6.07 mmol) in methylene chloride (5 mL). The cooling bath was removed, and the mixture was stirred overnight at room temperature. It was then diluted with methylene chloride, washed with 1N hydrochloric acid, saturated NaHCO$_3$, saturated brine solution, dried (Na$_2$SO$_4$), and evaporated. The methyl ester was obtained pure by silica gel chromatography eluting with 10% acetone in hexane; yield 1.49 g. It was then taken up in ethanol (50 mL) and treated with 0.2 N sodium hydroxide (26.6 mL) for 1.5 hours at room temperature. The mixture was acidified with glacial acetic acid, concentrated, the residue taken up in methylene chloride, washed with water, saturated brine solution, dried (Na$_2$SO$_4$), and evaporated to give the title compound; yield 1.4 g.

400 MHz $^1$H NMR (CD$_3$OD): δ 1.80–2.15 (m, 4H); 3.35–4.45 (m, 2H); 4.30 (dd, 1H); 7.76 (m, 1H); 7.83 (m, 2H).

Step C: N-(3,5-Dichlorobenzenesulfonyl)-(L)-prolyl-(L)-4-iodophenylalanine, tert-butyl ester.

To a solution of N-(3,5-dichlorobenzenesulfonyl)-(L)-proline (386 mg, 1.19 mmol) in methylene chloride (23 mL) were added 1-hydroxybenzotriazole (241 mg, 1.79 mmol), N-methylmorpholine (0.33 mL, 2.98 mmol), and 4-iodo-(L)-phenylalanine tert-butyl ester hydrochloride (458 mg, 1.19 mmol). After cooling in an ice-bath for 5 minutes, 1-(3-dimethylaminopropyl)-3-ethylcarbodiimide hydrochloride (EDC) (274 mg, 1.43 mmol) was added. After 15 minutes, the cooling bath was removed, and the mixture was stirred overnight under a nitrogen atmosphere. The mixture was diluted with methylene chloride, washed with water, 1N HCl, saturated NaHCO$_3$ solution, saturated brine solution, dried (MgSO$_4$), and evaporated. Silica gel chromatography eluting with 20% ethyl acetate in hexane afforded pure title compound; yield 651 mg (84%).

MS:m/e653(M+1); 400 MHz $^1$H NMR (CD$_3$OD): δ 1.45 (s, 9H); 1.65–1.85 (m, 4H); 3.0 (dd, 1H); 3.13 (dd, 1H); 3.45 (m, 1H); 4.20 (m, 1H); 4.55 (dd, 1H); 7.05 (d, 2H); 7.64 (d, 2H); 7.80 (s, 3H).

Step D: N-(3,5-Dichlorobenzenesulfonyl)-(L)-prolyl-(L)-4-(4-fluorophenyl)phenylalanine, tert-butyl ester.

To a solution of N-(3,5-dichlorobenzenesulfonyl)-(L)-prolyl-4-iodo-(L)-phenylalanine tert-butyl ester (100 mg, 0.15 mmol) in toluene (1 mL) and ethanol (0.5 mL) were added 4-fluorobenzeneboronic acid (24 mg, 0.16 mmol), potassium bromide (20 mg, 0.17 mmol), 2M Na$_2$CO$_3$ (0.20 mL, 0.38 mmol), and tetrakis(triphenylphosphine)palladium (9 mg, 0.008 mmol). The mixture was stirred for 1.5 hours at 95° C. under a nitrogen atmosphere, allowed to cool to room temperature, diluted with ethyl acetate, washed twice with 1N sodium hydroxide, once with saturated brine solution, dried (MgSO$_4$), and evaporated. The title compound was obtained pure by silica gel chromatography eluting with 10% acetone in hexane; yield 36 mg (38%).

MS: m/e 621 (M+H); 638 (M+H+NH$_3$); 400 MHz $^1$H NMR (CD$_3$OD): δ 1.47 (s, 9H); 1.65–1.87 (m, 4H); 3.08

(dd, 1H); 3.20 (dd, 1H); 3.45 (m, 1H); 4.24 (dd, 1H); 4.63 (dd, 1H); 7.15 (t, 2H); 7.35 (d, 2H); 7.54 (d, 2H); 7.57 (m, 2H); 7.77–7.80 (m, 3H).

Step E: N-(3,5-Dichlorobenzenesulfonyl)-(L)-prolyl-(L)-4-(4'-fluorophenyl)phenylalanine.

A cooled solution of N-(3,5-dichlorobenzenesulfonyl)-(L)-prolyl-4-(4-fluorophenyl)-(L)-phenylalanine tert-butyl ester (36 mg, 0.055 mmol) in methylene chloride (1.4 mL) was treated with trifluoroacetic acid (0.28 mL, 3.63 mmol). The cooling bath was removed, and the mixture was stirred overnight at room temperature. The reaction mixture was then evaporated, coevaporated with methylene chloride (3×), toluene (2×), and finally methanol. The product was dried under high vacuum; yield 32 mg.

MS: m/e 565(M+H); 582(M+H+NH3); 400 MHz $^1$H NMR (CD$_3$OD): δ 1.60–1.90 (m, 4H); 3.10 (dd, 1H); 3.42 (m, 1H); 4.22 (t, 1H); 4.73 (m, 1H); 7.11 (t, 2H); 7.34 (d, 2H); 7.52 (d, 2H); 7.56 (m, 2H); 7.72–7.79 (m, 3H).

EXAMPLE 4 (L-817,757)

N-(3,5-Dichlorobenzenesulfonyl)-(L-)-prolyl-(L)-4-(2'-thienyl)-phenylalanine

This compound was prepared in a similar fashion as Example 3 using 2-thienyl-boronic acid in Step D.

MS: m/e=553 (M+H$^+$); 570 (M+1+NH$_{4+}$).

EXAMPLE 5 (L-817,758)

N-(3,5-Dichlorobenzenesulfonyl)-(L-)-prolyl-(L)-4-(3'-thienyl)-phenylalanine

This compound was prepared in a similar fashion as Example 3 using 3-thienyl-boronic acid in Step D.

MS: m/e=553 (M+H$^+$); 570 (M+NH$_4^+$).

EXAMPLE 6 (L-817,897)

N-(3,5-Dichlorobenzenesulfonyl)-(L-)-prolyl-(L)-4-(4'-trifluoromethyl-phenyl)-phenylalanine This compound was prepared in a similar fashion as Example 3 using 4-trifluoromethylbenzene boronic acid Step D.

MS: m/e=615 (M+H$^+$); 632 (M+NH$_4^+$).

EXAMPLE 7 (L-817,986)

N-(3,5-Dichlorobenzenesulfonyl)-(L-)-prolyl-(L)-4-(2'-methoxy-phenyl)-phenylalanine This compound was prepared in a similar fashion as Example 3 using 2-methoxybenzene boronic acid Step D.

MS: m/e=577 (M+H$^+$); 594 (M+NH$_4^+$).

EXAMPLE 8 (L-821,051)

N-(3,5-Dichlorobenzenesulfonyl)-(L-)-prolyl-(L)-4-(2'-formyl-phenyl)-phenylalanine This compound was prepared in a similar fashion as Example 3 using 2-formyl-benzene boronic acid Step D.

MS: m/e=575 (M+H$^+$); 592 (M+NH$_4^+$).

The following compounds were also prepared by the procedures described in Example 3 using the appropriate amino acid and acyl or sulfonyl chloride derivatives in Step B and the appropropriate boronic acid derivative in Step D:

| Example Number | | Name | Mass Spectrum* |
|---|---|---|---|
| 821119 | (9) | N-(3-fluorobenzenesulfonyl)-(L)-prolyl-(L)-4-(3'-thienyl)phenylalanine; | 503 520 |
| 821245 | (10) | N-(3,5-dichlorobenzenesulfonyl)-(L)-prolyl-(L)-4-(2',6'-difluorophenyl)phenylalanine; | 600 |
| 821302 | (11) | N-(3,5-dichlorobenzenesulfonyl)-(L)-prolyl-(L)-4-(2'-hydroxymethylphenyl)phenylalanine; | 594 |
| 821333 | (12) | N-(3,5-dichlorobenzenesulfonyl)-(L)-prolyl-(L)-4-(4'-methylphenyl)phenylalanine; | 561 578 |
| 821646 | (13) | N-(3,5-dichlorobenzenesulfonyl)-(L)-prolyl-(L)-4-(2'-carboxyphenyl)phenylalanine; | 608 |
| 821647 | (14) | N-(3,5-dichlorobenzenesulfonyl)-(L)-prolyl-(L)-4-(2'-methoxycarbonylphenyl)phenylalanine; | 605 622 |
| 821848 | (15) | N-(3,5-dichlorobenzenesulfonyl)-(L)-prolyl-(L)-4-(3'-formylphenyl)phenylalanine; | 575 592 |
| 821849 | (16) | N-(3,5-dichlorobenzenesulfonyl)-(L)-prolyl-(L)-4-(3'-aminophenyl)phenylalanine; | 562 579 |
| 821965 | (17) | N-(3,5-dichlorobenzenesulfonyl)-(L)-prolyl-(L)-4-(2'-methylphenyl)phenylalanine; | 561 578 |
| 823156 | (18) | N-(3,5-dichlorobenzenesulfonyl)-(L)-prolyl-(L)-4-(3'-acetamidophenyl)phenylalanine; | 621 |
| 823183 | (19) | N-(3,5-dichlorobenzenesulfonyl)-(L)-prolyl-(L)-4-(2'-fluorophenyl)phenylalanine; | 565 582 |
| 823255 | (20) | N-(3,5-diclorobenzenesulfonyl)-(L)-prolyl-(L)-4-(3'-carboxyphenyl)phenylalanine; | 608 |
| 823256 | (21) | N-(3,5-dichlorobenzenesulfonyl)-(L)-prolyl-(L)-4-(3'-methoxycarbonylphenyl)phenylalanine; | 622 |
| 823257 | (22) | N-(3,5-dichlorobenzenesulfonyl)-(L)-prolyl-(L)-4-(2',4'-dichlorophenyl)phenylalanine; | 632 |
| 825677 | (23) | N-(3,5-dichlorobenzenesulfonyl)-(L)-prolyl-(L)-4-(2' formyl-3'-thienyl)phenylalanine; | 581 |

-continued

| Example Number | | Name | Mass Spectrum* |
|---|---|---|---|
| 823448 | (24) | N-(3,5-dichlorobenzenesulfonyl)-(L)-2(S)-methyl-prolyl-(L)-4-(4'-fluorophenyl)phenylalanine | 596 |
| 823177 | (25) | N-(3,5-dichlorobenzenesulfonyl)-(L)-2(S)-methyl-prolyl-(L)-4-(2'-formylphenyl)phenylalanine | 606 |
| 823178 | (26) | N-(3,5-dichlorobenzenesulfonyl)-(L)-2(S)-methyl-prolyl-(L)-4-(2'-(hydroxymethyl)phenyl)phenylalanine | 608 |
| 828566 | (27) | N-(3,5-dichlorobenzenesulfonyl)-(L)-2(S)-methyl-prolyl-(L)-4-(2'-cyanophenyl)phenylalanine | 603 |
| 829166 | (28) | N-(benzenesulfonyl)-(L)-2(S)-methyl-prolyl-(L)-4-(2'-formylphenyl)phenylalanine | 521 |
| 829564 | (29) | N-(benzenesulfonyl)-(L)-2(S)-methyl-prolyl-(L)-4-(2'-methoxyphenyl)phenylalanine | 523 |
| 835243 | (30) | N-(3-chlorobenzenesulfonyl)-(L)-2(S)-methyl-prolyl-(L)-4-(2'-methylthiophenyl)phenylalanine | 590.3 |
| 837457 | (31) | N-(3,5-dichlorobenzenesulfonyl)-(L)-2(S)-methyl-prolyl-(L)-4-(2'-methoxyphenyl)-2-thienyl-alanine | 614.3 |
| 840677 | (32) | N-(3,5-dichlorobenzenesulfonyl)-(D)-2(R)-methyl-prolyl-(D)-4-(2'-cyanophenyl)phenylalanine | 603.0 |
| 842378 | (33) | N-(3,5-dichlorobenzenesulfonyl)-(D)-2(R)-methyl-prolyl-(L)-4-(2'-cyanophenyl)phenylalanine | 603 |
| 832158 | (34) | N-(3,5-dichlorobenzenesulfonyl)-(L)-2(S)-methyl-prolyl-(L)-4-(2'-methoxyphenyl)phenylalanine | 591 |
| 835250 | (35) | N-(3,5-dichlorobenzenesulfonyl)-(L)-2(S)-methyl-prolyl-(L)-4-(2'-methylthio-phenyl)phenylalanine | 607 |
| 837017 | (36) | N-(3,5-dichlorobenzenesulfonyl)-(L)-3(R)-methyl-prolyl-(L)-4-(2'-methoxyphenyl)phenylalanine, methyl ester | 617.4 |
| 829767 | (37) | N-(benzenesulfonyl)-(L)-4(R)-amino-prolyl-(L)-4-(2'-cyanophenyl)phenylalanine | 519 |
| 829768 | (38) | N-(benzenesulfonyl)-(L)-4(S)-amino-prolyl-(L)-4-(2'-cyanophenyl)phenylalanine | 519 |

*m/e, ($M^+$) or ($M + H^+$) or ($M + NH_4^+$).

EXAMPLE 39 L-837216

(3,5-dichlorobenzenesulfonyl)-(L)-2(S)-methyl-prolyl-(L)-4-(2'-rifluoromethoxyphenyl)phenylalanine Step A: 2-Trifluoromethoxybenzeneboronic Acid.

A solution of 2-bromo-trifluoromethoxybenzene (1.0 g, 4.15 mmol) in dry tetrahydrofuran (20 mL) was cooled to −70° C. A 2.5 M solution of n-butyllithium in hexanes (2.0 mL, 4.98 mmol) was slowly added over a 5 min period, keeping the temperature below −65° C. After stirring at −70° C. for 30 min, triisopropylborate (1.5 mL, 6.22 mmol) was added over a 5 min period. After stirring at −70° C. for 30 min, the solution was stirred at room temperature overnight. An aqueous solution of 2N HCl (10 mL) was added and the mixture stirred for 2 hr. The solution was diluted with ethyl acetate (100 mL). The layers were separated and the organic layer successively washed with 2N HCl (2×25 mL), water (1×25 mL), and saturated salt solution (1×25 mL). The solution was dried over anhydrous magnesium sulfate, filtered and concentrated by rotoevaporation to a pale crystalline solid which was triturated with a little hexanes and filtered. The filtrate was concentrated to a white solid. The two solids were combined to yield 434 mg of the title compound which was used without further purification in the subsequent reaction.

Steps B,C: N-(3,5-dichlorobenzenesulfonyl)-(L)-2(S)-methyl-prolyl-(L)-4-(2'-trifluoromethoxyphenyl)phenylalanine Following the procedures described in Example 3, Steps D and E, trifluoromethoxybenzene boronic acid was converted to N-(3,5-dichlorobenzenesulfonyl)-(L)-2(S)-methyl-prolyl-(L)-4-(2'-trifluoromethoxyphenyl)phenylalanine.

MS: m/e=645 ($M+H^+$); 662 ($M+NH_4^+$).

EXAMPLE 40 L-829769

N-(Benzenesulfonyl)-(L)-4(R)-benzoylamino-prolyl-(L)-4-(2'-cyanophenyl)phenylalanine Step A: N-(Benzenesulfonyl)-(L)-4(R)-benzoylamino-prolyl-(L)-4-(2'-cyanophenyl)phenylalanine t-butyl ester.

To an ice-cooled solution of N-(benzenesulfonyl)-(L)-4(R)-amino-prolyl-(L)-4-(2'-cyanophenyl)phenylalanine, t-butyl ester (from the preparation of Example 37) (6.3 mg, 0.011 mmol) in methylene chloride was sequentially added N-methylmorpholine (2.5 μL, 0.022 mmol) and benzoyl chloride (2 μL, 0.016 mmol). After stirring at 0° C. for 2 hr, the reaction was quenched with methanol (0.5 mL). The volatiles were removed by rotoevaporation and the residue purified by flash column chromatography on silica gel eluted with 50% ethyl acetate in hexanes to yield the title compound (6.8 mg, 91% yield).

MS: m/e=696 ($M+NH_4+$).

Step B: N-(Benzenesulfonyl)-(L)-4(R)-benzoylamino-prolyl-(L)-4-(2'-cyanophenyl)phenylalanine.

The tert-butyl ester from Step A was hydrolyzed according to the procedure described in Example 3, Step E to yield N-(benzenesulfonyl)-(L)-4(R)-benzoylamino-prolyl-(L)-4-(2'-cyanophenyl)phenylalanine.

MS: m/e=640 ($M+NH_4+$).

The following compounds were also prepared by the procedures described in Example 40 using the appropriate 4-amino-proline derivative and the appropriate acyl chloride in Step A:

| EXAMPLE NUMBER | | Name | MS* |
|---|---|---|---|
| 829770 | (41) | N-(benzenesulfonyl)-(L)-4(S)-benzoylamino-prolyl-(L)-4-(2'-cyanophenyl)phenylalanine | 623 |
| 829771 | (42) | N-(benzenesulfonyl)-(L)-4(R)-phenylacetylamino-prolyl-(L)-4-(2'-cyanophenyl)phenylalanine | 654 |
| 829772 | (43) | N-(benzenesulfonyl)-(L)-4(S)-phenylacetylamino-prolyl-(L)-4-(2'-cyanophenyl)phenylalanine | 654 |

*m/e, (M$^+$) or (M + H$^+$) or (M + NH$_4^+$).

EXAMPLE 44

N-(3,5-Dichlorobenzenesulfonyl)-(L)-prolyl-(L)-N-methyl-4-(2'-methoxyphenyl)phenylalanine Step A: N-BOC-N-methyl-4-iodophenylalanine.

Following the procedure of Boger and Yohannes (J. Org. Chem. 53, 487 (1988), a solution of N-BOC-4-iodophenylalanine (391 mg, 1 mmol) and methyl iodide (156 µL, 2.5 mmol) in tetrahydrofuran (5 mL) at 0° C. was added 60% sodium hydride in oil suspension (100 mg, 2.5 mmol). The resulting mixture was stirred at 0° C. for 1 hr and then at room temperature for 16 hr. Added dimethylformamide (1 mL) and additional methyl iodide (156 µL, 2.5 mmol) and 60% sodium hydride (100 mg, 2.5 mmol) and heated at 75° C. overnight. The reaction was worked up as described in the reference to yield N-BOC-N-methyl-4-iodophenylalanine.

Steps B–F: N-(3,5-Dichlorobenzenesulfonyl)-(L)-prolyl-(L)-N-methyl-4-(2'-methoxyphenyl)phenylalanine Following the procedures described in Example 3, Steps A–E, N-BOC-N-methyl-4-iodophenylalanine was converted N-(3,5-dichlorobenzenesulfonyl)-(L)-prolyl-(L)-N-methyl-4-(2'-methoxyphenyl)phenylalanine.

MS: m/e=608.3 (M+NH$_4^+$).

The following compound was prepared by the procedures described in Example 44 using (L)-3(S)-methyl-proline:

| EXAMPLE NUMBER | | Name | MS* |
|---|---|---|---|
| 331615 | (45) | N-(3,5-dichlorobenzenesulfonyl)-(L)-3(S)-methyl-prolyl-(L)-N-methyl-4-(2'-methoxyphenyl)phenylalanine | 622.4 |

*m/e, (M$^+$) or (M + H$^+$) or (M + NH$_4^+$).

EXAMPLE 46 (L-823,420)

N-(3-Fluorobenzenesulfonyl)-(L)-prolyl-(L)-4-(2'-cyanophenyl)phenylalanine

Step A: N-(3-Fluorobenzenesulfonyl)-(L)-prolyl-(L)-4-trimethylstannylphenylalanine, tert-butyl ester.

A solution of N-(3-fluorobenzenesulfonyl)-(L)-prolyl-(L)-4-iodophenylalanine, tert-butyl ester (prepared according to the method described in Example 3) (1.0 g, 1.53 mmol), hexamethylditin (411 µL, 2.14 mmol), triphenylphosphine (8 mg, 0.03 mmol), lithium chloride (71 mg, 1.68 mmol), and tetrakis(triphenylphosphine)palladium(0) (88 mg, 0.077 mmol) in 1,4-dioxane (10 mL) was heated to 95° C. under a dry nitrogen atmosphere for 1.5 hr. The solution was cooled and diluted with ethyl acetate (100 mL) and successively washed with 1N sodium hydroxide solution (2x) and saturated salt solution (1x). After drying over anhydrous magnesium sulfate, the solution was filtered and the solvent removed by rotoevaporation. The residue was purified by silica gel column chromatography eluted with 10% acetone in hexanes to yield N-(3-fluorobenzenesulfonyl)-(L)-prolyl-(L)-4-(trimethylstannyl)phenylalanine, tert-butyl ester (577 mg, 54% yield).

MS: m/e=658 (M+18; NH$_4^+$).

Step B: N-(3-Fluorobenzenesulfonyl)-(L)-prolyl-(L)-4-(2'-cyanophenyl)phenylalanine, tert-butyl ester.

To a solution of N-(3-fluorobenzenesulfonyl)-(L)-prolyl-(L)-4-(trimethylstannyl)phenylalanine, tert-butyl ester (50 mg, 0.078 mmol) in toluene (2 mL) was added 2-bromobenzonitrile (14 mg, (0.078 mmol). The solution was degassed under a dry nitrogen atmosphere (3x). Dichlorobis(triphenylphosphine)palladium(II) (2 mg, 0.0023 mmol) was added and the reaction heated to 100° C. for 2 hr. Additional 2-bromobenzonitrile (7 mg, 0.039 mmol) and dichlorobis(triphenylphosphine)palladium(II) (2 mg, 0.0023 mmol) was added and the reaction continued to be heated for 1 hr. The reaction was cooled and ethyl acetate added. The solution was washed with water and saturated salt solution and dried over anhydrous magnesium sulfate. The solvent was removed by rotoevaporation and the residue purified by silica gel column chromatography eluted with 20% acetone in hexanes to yield N-(3-fluorobenzenesulfonyl)-(L)-prolyl-(L)-4-(2'-cyanophenyl)phenylalanine, tert-butyl ester (24 mg, 53% yield).

Step C: N-(3-Fluorobenzenesulfonyl)-(L)-prolyl-(L)-4-(2'-cyanophenyl)phenylalanine To a solution of N-(3-fluorobenzenesulfonyl)-(L)-prolyl-(L)-4-(2'-cyanophenyl)phenylalanine, tert-butyl ester (24 mg, 0.042 mmol) in ice cooled methylene chloride (1 mL) was added trifluoroacetic acid (198 µL, 2.58 mmol). The ice bath was removed and the solution stirred at room temperature overnight. The solvent was removed by rotoevaporation and then coevaporated with methylene chloride (2x), toluene (2x) and methanol (2x) to yield N-(3-fluorobenzenesulfonyl)-(L)-prolyl-(L)-4-(2'-cyanophenyl)phenylalanine as a solid (21.5 mg, 98% yield).

MS: m/e 522 (M+1), 539 (M+18; NH$_4^+$). 400 MHz $^1$H NMR (CD$_3$OD): δ 1.51–1.87 (m, 4H); 3.12–3.26 (m, 2H); 4.17 (dd, 1H); 4.78 (m, 1H); 7.41–7.81 (m, 12H); 8.17 (d, 1H).

The following compounds were also prepared by analogous procedures described in Example 46 using the appropriate acylating or sulfonylating agent in the preparation of the starting material in Step A and the appropriate aryl halide derivative in Step B:

| EXAMPLE NUMBER | | Name | MS* |
|---|---|---|---|
| 823829 | (47) | N-(3,5-dichlorobenzenesulfonyl)-(L)-prolyl-(L)-4-(4'-fluoro-2'-methoxyphenyl)phenylalanine | 612 |
| 825251 | (48) | N-(3,5-dichlorobenzenesulfonyl)-(L)-prolyl-(L)-4-(2'-cyanophenyl)phenylalanine | 589 |
| 825953 | (49) | N-(3,5-dichlorobenzenesulfonyl)-(L)-prolyl-(L)-4-(2'-methylthio-phenyl)phenylalanine | 610 |
| 828252 | (50) | N-(3,5-dichlorobenzenesulfonyl)-(L)-prolyl-(L)-4-(2'-(5-methyl-1,3,4-oxadiazol-2-yl-phenyl)phenylalanine | 629 |
| 828335 | (51) | N-(3,5-dichlorobenzenesulfonyl)-(L)-prolyl-(L)-4-(2-methyl-5-trifluoromethyl-benzoxazol-7-yl)phenylalanine | 670 |
| 828336 | (52) | N-(3,5-dichlorobenzenesulfonyl)-(L)-prolyl-(L)-4-(2-methyl-6-(5-trifluoromethyl-tetrazol-1-yl)-benzoxazol-4-yl)phenylalanine | 738 |
| 828337 | (53) | N-(3,5-dichlorobenzenesulfonyl)-(L)-prolyl-(L)-4-(2-methyl-5-(5-trifluoromethyl-tetrazol-1-yl)-benzoxazol-7-yl)phenylalanine | § seeNMR below |
| 829023 | (54) | N-(3,5-dichlorobenzenesulfonyl)-(L)-prolyl-(L)-4-(3-pyridyl)phenylalanine | 548 |
| 829096 | (55) | N-(3,5-dichlorobenzenesulfonyl)-(L)-prolyl-(L)-4-(2-pyridyl)phenylalanine | 548 |
| 829163 | (56) | N-(3,5-dichlorobenzenesulfonyl)-(L)-prolyl-(L)-4-(5-pyrimidinyl)phenylalanine | 549 |
| 829337 | (57) | N-(3,5-dichlorobenzenesulfonyl)-(L)-prolyl-(L)-4-(3'-cyanophenyl)phenylalanine | 589 |
| 829568 | (58) | N-(3,5-dichlorobenzenesulfonyl)-(L)-prolyl-(L)-4-(2-methyl-benzoxazol-4-yl)phenylalanine | 602 |
| 829569 | (59) | N-(3,5-dichlorobenzenesulfonyl)-(L)-prolyl-(L)-4-(6-acetamido-2-methyl-benzoxazol-4-yl)phenylalanine | 659 |
| 829728 | (60) | N-(benzenesulfonyl)-(L)-prolyl-(L)-4-(2-pyridyl)phenylalanine | 480 |
| 829515 | (61) | N-(3,5-dichlorobenzenesulfonyl)-(L)-3(S)-methylprolyl-(L)-4-(2'-cyanophenyl)phenylalanine | 603 |
| 832000 | (62) | N-(benzenesulfonyl)-(L)-2(S)-methyl-prolyl-(L)-4-(2'-cyanophenyl)phenylalanine | 535.3 |
| 832665 | (63) | N-(3-chlorobenzenesulfonyl)-(L)-2(S)-methyl-prolyl-(L)-4-(2'-cyanophenyl)phenylalanine | 569.4 |
| 835242 | (64) | N-(3-chlorobenzenesulfonyl)-(L)-2(S)-methyl-prolyl-(L)-4-(5-pyrimidinyl)phenylalanine | 557.5 |
| 835633 | (65) | N-(3-trifluoromethylbenzenesulfonyl)-(L)-2(S)-methyl-prolyl-(L)-4-(2'-cyanophenyl)phenylalanine | 603.5 |
| 832455 | (66) | N-(3,5-dichlorobenzenesulfonyl)-(L)-2(S)-methyl-prolyl-(L)-4-(3-pyridyl)phenylalanine | 562 |
| 832512 | (67) | N-(3,5-dichlorobenzenesulfonyl)-(L)-2(S)-methyl-prolyl-(L)-4-(5-pyrimidinyl)phenylalanine | 562 |
| 832834 | (68) | N-(3,5-dichlorobenzenesulfonyl)-(L)-2(S)-methyl-prolyl-(L)-4-(3'-cyano-phenyl)phenylalanine | 603 |
| 835249 | (69) | N-(3,5-dichlorobenzenesulfonyl)-(L)-2(S)-methyl-prolyl-(L)-4-(5'-fluoro-2'-methoxy-phenyl)phenylalanine | 609 |
| 835823 | (70) | N-(3,5-dichlorobenzenesulfonyl)-(L)-2(S)-methyl prolyl-(L)-4-(2'-methoxy-5'-trifluoromethyl-phenyl)phenylalanine | 659 |
| 837420 | (71) | N-(3,5-dichlorobenzenesulfonyl)-(L)-2(S)-methyl-prolyl-(L)-4-(2-pyridyl)phenylalanine | 562 |
| 837910 | (72) | N-(3,5-dichlorobenzenesulfonyl)-(L)-2(S)-methyl-prolyl-(L)-4-(3'-fluoro-2'-cyano-phenyl)phenylalanine | 604 |
| 840141 | (73) | N-(3,5-dichlorobenzenesulfonyl)-(L)-2(S)-methyl-prolyl-(L)-4-(2'-trifluoromethylsulfonyl-phenyl)phenylalanine | 710 |
| 840390 | (74) | N-(3,5-dichlorobenzenesulfonyl)-(L)-2(S)-methyl prolyl-(L)-4-(2-thiazolyl)phenylalanine | 568 |
| 840702 | (75) | N-(3,5-dichlorobenzenesulfonyl)-(L)-2(S)-methyl-prolyl-(L)-4-(5-( 1H,3H-pyrimidine-2,4-dione)phenylalanine | 612 |
| 842725 | (76) | N-(3,5-dichlorobenzenesulfonyl)-(L)-2(S)-methyl-prolyl-(L)-4-(4'-fluoro-3'-cyano-phenyl)phenylalanine | 623 |
| 842726 | (77) | N-(3,5-dichlorobenzenesulfonyl)-(L)-2(S)-methyl-prolyl-(L)-4-(2'-fluoro-5'-cyano-phenyl)phenylalanine | 621 |
| 835422 | (78) | N-(3,5-dichlorobenzenesulfonyl)-(L)-2(S)-methyl-prolyl-(L)-4-(1-methyl-7-indolyl)phenylalanine | 631 |

-continued

| EXAMPLE NUMBER | | Name | MS* |
|---|---|---|---|
| 835599 | (79) | N-(3,5-dichlorobenzenesulfonyl)-(L)-2(S)-methyl-prolyl-(L)-4-(7-indolyl)phenylalanine | 617 |
| 837084 | (80) | N-(3,5-dichlorobenzenesulfonyl)-(L)-2(S)-methyl-prolyl-(L)-4-(benzthiazol-4-yl)phenylalanine | 618 |

*m/e, (M$^+$) or (M + H$^+$) or (M + NH$_4{}^+$).

EXAMPLE 81 L-832485

N-(3,5-dichlorobenzenesulfonyl)-(L)-2(S)-methyl-prolyl-(L)-4-(benzoxazol-4-yl)phenylalanine Step A: 6-Bromo-2-anisidine.

To a cooled solution of 2-anisidine (2.7 mL, 23.7 mmol) in cetic acid (20 mL) at 10° C. was slowly added a solution of bromine (1.22 mL, 23.7 mmol) in acetic acid (10 mL) over a 10 min period. After stirring for 10 min, the solvents were removed by rotoevaporation and the residue dissolved in ethyl acetate. This solution was successively washed with saturated sodium bicarbonate solution and dried over anhydrous magnesium sulfate. After filtering, the solvents were removed by rotoevaporation and the product purified by flash column chromatography on silica gel eluted with 45% methylene chloride in hexanes to yield 3.44 g (72% yield) of the title compound.

Step B: 2-Amino-3-bromophenol.

To an ice cooled solution of 6-bromo-2-anisidine (1.01 g, 5 mmol) in methylene chloride (30 mL) was slowly added a 1.0 M solution of boron tribromide in methylene chloride (10 mL, 10 mmol) via syringe. The reaction was slowly warmed to room temperature and stirred overnight. Methanol (10 mL) was added and the solvents removed by rotoevaporation to give the title compound (0.87 g, 92% yield).

Step C: 4-Bromobenzoxazole.

Following a literature procedure (Org. Prep. & Proc. Int. 22(5), 613 (1990)), a solution of 2-amino-3-bromophenol (800 mg, 4.25 mmol) and trimethylformate (0.685 mL, 6.25 mmol) in methanol (1.25 mL) was treated with concentrated hydrochloric acid (0.01 mL). The flask was fitted with a short path distillation apparatus. The temperature of the solution was slowly raised to 90° C. and maintained until the methanol had finished distilling. Upon cooling, the residue crystallized and was dissolved in diethyl ether (70 mL). This solution was successively washed with 5% sodium hydroxide solution and water and dried over anhydrous magnesium sulfate. After filtering, the solvents were removed by rotoevaporation and the residue was purified by flash column chromatography on silica gel eluted with 20% ethyl acetate in hexanes to yield the title compound (550 mg, 65% yield).

Steps D–E: N-(3,5-dichlorobenzenesulfonyl)-(L)- 2(S)-methyl-prolyl-(L)-4-(benzoxazol-4-yl)phenylalanine.

4-Bromobenzoxazole was reacted with N-(3,5-dichlorobenzenesulfonyl)-(L)-2(S)-methyl-prolyl-(L)-4-(trimethylstannyl)phenylalanine according to the procedures described in Example 46, Steps B and C to yield the title compound.

MS: m/e=602 (M+H$^+$).

EXAMPLE 82 L-832697

N-(3,5-Dichlorobenzenesulfonyl)-(L)-2(S)-methyl-prolyl-(L)-4-(2-methyl-benzoxazol-4-yl) phenylalanine This compound was prepared in a similar fashion as Example 81 using 4-bromo-2-methyl-benzoxazole prepared from 2-amino-3-bromophenol and trimethylorthoacetate.

MS: m/e=616 (M+H$^+$).

EXAMPLE 83 L-333621

N-(3,5-Dichlorobenzenesulfonyl)-(L)-2(S)-methyl-prolyl-(L)-4-(2-trifluoromethyl-benzoxazol-4-yl) phenylalanine Step A: 4-Bromo-2-trifluoromethyl-benzoxazole.

A solution of 2-amino-3-bromophenol (480 mg, 2.6 mmol), polyphosphoric ester (PPE, 3.4 g) and trifluoroacetic acid (0.88 mL, 11.5 mmol) was heated to 100° C. under a nitrogen atmosphere overnight. A reflux condenser was added as was fresh PPE and the reaction heated to 120° C. for 8 hr. The reaction was cooled and diluted with methylene chloride. The solvent was removed by rotoevaporation. The residue was dissolved in fresh methylene chloride and successively washed with 2N sodium hydroxide solution and saturated salt solution. After drying over anhydrous magnesium sulfate and filtering, the solvent was removed by rotoevaporation. The residue was purified by flash column chromatography in silica gel eluted with 15% acetone in hexanes to yield the title compound (110 mg, 16% yield).

Steps B–C N-(3,5-dichlorobenzenesulfonyl)-(L)-2(S)-methyl-prolyl-(L)-4-(2-trifluoromethyl-4-benzoxazolyl) phenylalanine.

This compound was prepared in a similar fashion as Example 46, Steps B and C using 4-bromo-2-trifluoromethyl-benzoxazole.

MS: m/e=671 (M+H$^+$).

EXAMPLE 84 L-835536

N-(3,5-dichlorobenzenesulfonyl)-(L)-2(S)-methyl-prolyl-(L)-4-(2'-isopropyloxy-phenyl)phenylalanine Step A: 2-Bromo-isopropyloxybenzene.

2-Bromophenol (500 mg, 2.9 mmol) was dissolved in dry dimethylformamide (5 mL) under a dry nitrogen atmosphere. Powdered dry cesium carbonate (1.41. g, 4.34 mmol) was added, followed by the addition of 2-bromopropane (404 μL, 4.05 mmol) over a 2 min period. The mixture was stirred at room temperature overnight. Water (50 mL) was added and the mixture extracted with ethyl acetate (2×50 mL). The combined extracts were successively washed with water (25 mL) and saturated salt solution (25 mL) and dried over anhydrous magnesium sulfate. The dried solution was filtered and the solvents removed rotoevaporation to yield the title compound as an oil (522 mg, 84% yield).

Steps B–D: N-(3,5-dichlorobenzenesulfonyl)-(L)-2(S)-methyl-prolyl-(L)-4-(2'-isopropyloxy-phenyl) phenylalanine.

Following the procedures described in Example 46, Steps A–C, 2-bromo-isopropyloxybenze was converted to N-(3, 5-dichlorobenzenesulfonyl)-(L)-2(S)-methyl-prolyl-(L)-4-(2'-isopropyloxy-phenyl)phenylalanine.

MS: m/e=619 (M+H$^+$), 636 (M+NH$_4^+$).

EXAMPLE 85(L-825473)

N-(3,5-Dichlorobenzenesulfonyl)-(L)-prolyl-(L)-4-(2'-(tetrazol-5-yl)phenyl)phenylalanine Step A: N-(3,5-Dichlorobenzenesulfonyl)-(L)-prolyl-(L)-4-(2'-(tetrazol-5-yl)phenyl)phenylalanine, tert-butyl ester.

Trimethyltinazide (115 mg, 0.556 mmol) was added to a solution of N-(3,5-dichlorobenzenesulfonyl)-(L)-prolyl-(L)-4-(2'-cyanophenyl)phenylalanine, tert-butyl ester (prepared according to the procedures described in Example 27, Step B) (100 mg, 0.159 mmol) in toluene under dry nitrogen atmosphere. The solution was heated to 115° C. for 18 hr. Upon cooling to room temperature, the solvent was removed by rotoevaporation and the residue dissolved in ethyl acetate. The solution was successively washed with 5N hydrochloric acid and saturated salt solution and dried over anhydrous sodium sulfate. The mixture was filtered and the solvent removed by rotoevaporation. The residue was purified by flash column chromatography on silica gel eluted with 2–5% methanol in methylene chloride to yield N-(3, 5-dichlorobenzenesulfonyl)-(L)-prolyl-(L)-4-(2'-(tetrazol-5-yl)phenyl)phenylalanine, tert-butyl ester (32 mg, 30% yield).

MS: m/e 671 (M+1).

Step B: N-(3,5-Dichlorobenzenesulfonyl)-(L)-prolyl-(L)-4-(2'-(tetrazol-5-yl)phenyl)phenylalanine.

Trifluoroacetic acid (0.227 mL, 2.95 mmol) was added to a solution of N-(3,5-dichlorobenzenesulfonyl)-(L)-prolyl-(L)-4-(2'-(tetrazol-5-yl)phenyl)phenylalanine, tert-butyl ester (32 mg, 0.048 mmol) in methylene chloride (1.2 mL) and stirred for 18 hr at room temperature. The solution was concentrated by rotoevaporation to a solid and then successively co-evaporated with methlene chloride, toluene and methanol. The crude solid was purified by flash column chromatography on silica gel eluted with 0.5% acetic acid in 5%methanol/methylene chloride to give N-(3,5-dichlorobenzenesulfonyl)-(L)-prolyl-(L)-4-(2'-(tetrazol-5-yl)phenyl)phenylalanine (15 mg).

MS: m/e 615 (M+1). 400 MHz $^1$H NMR (CD$_3$OD): δ 3.44 (m, 1H), 4.19 (t, 1H) 4.68 (t, 1H), 7.07 (d, 2H), 7.23 (d, 2H), 7.52 (m, 2H), 7.64 (m, 2H), 7.78 (m, 3H).

EXAMPLE 86(L-825951)

N-(3,5-Dichlorobenzenesulfonyl)-(L)-prolyl-(L)-4-(2'-(2-methyl-tetrazol-5-yl)phenyl)phenylalanine Step A. N-(3,5-Dichlorobenzenesulfonyl)-(L)-prolyl-(L)-4-(2'-(2-methyl-tetrazol-5-yl)phenyl)phenylalanine, tert-butyl ester Potassium carbonate (10 mg, 0.075 mmol) and methyl iodide (4.6 μL, 0.075 mmol) were added to a solution of N-(3,5-dichlorobenzenesulfonyl)-(L)-prolyl-(L)-4-(2'-(tetrazol-5-yl)phenyl)phenylalanine, tert-butyl ester (from Example 36, Step A) (33 mg, 0.049 mmol) in dimethylformamide and stirred at room temperature for 2 hr. The reaction was partioned between water and ethyl acetate and separated. The organic layer was successively washed with water and saturated salt solution and dried over anhydrous sodium sulfate. The solvent was removed by rotoevaporation and the crude solid purified by flash column chromatography on silica gel eluted with 10% acetone in hexanes. The component that eluted first proved to be N-(3,5-dichlorobenzenesulfonyl)-(L)-prolyl-(L)-4-(2'-(1-methyl-tetrazol-5-yl)phenyl)phenylalanine, tert-butyl ester (8 mg, 24% yield).

MS: m/e 685 (M+1).

The component that eluted second was N-(3,5-dichlorobenzenesulfonyl)-(L)-prolyl-(L)-4-(2'-(2-methyl-tetrazol-5-yl)phenyl)phenylalanine, tert-butyl ester (17 mg, 51% yield).

MS: m/e 685 (M+1).

Step B. N-(3,5-Dichlorobenzenesulfonyl)-(L)-prolyl-(L)-4-(2'-(2-methyl-tetrazol-5-yl)phenyl)phenylalanine.

Trifluoroacetic acid (56 μL, 0.72 mmol) was added to a solution of N-(3,5-dichlorobenzenesulfonyl)-(L)-prolyl-(L)-4-(2'-(2-methyl-tetrazol-5-yl)phenyl)phenylalanine, tert-butyl ester (8 mg, 0.012 mmol) in methylene chloride (0.5 mL) and stirred for 18 hr at room temperature. The solvent was removed by rotoevaporation and the crude solid successively co-evaporated with methylene chloride, toluene, and methanol to yield N-(3,5-dichlorobenzenesulfonyl)-(L)-prolyl-(L)-4-(2'-(2-methyl-tetrazol-5-yl)phenyl) phenylalanine as a white solid (6.5 mg, 86% yield).

MS: m/e 629 (M+1). 400 MHz $^1$H NMR (CD$_3$OD): δ 3.45 (m, 1H), 4.23 (t, 1H), 4.27 (s, 3H), 7.07 (d, 2H), 7.19 (d, 2H), 7.46 (m, 2H), 7.70 (d, 1H), 7.78 (d, 3H), 8.14 (d, 1H).

EXAMPLE 87 (L-825952)

N-(3,5-Dichlorobenzenesulfonyl)-(L)-prolyl-(L)-4-(2'-(3-methyl-tetrazol-5-yl)phenyl)phenylalanine Trifluoroacetic acid (120 μL, 1.54 mmol) was added to a solution of N-(3,5-dichlorobenzenesulfonyl)-(L)-prolyl-(L)-4-(2'-(3-methyl-tetrazol-5-yl)phenyl)phenylalanine, tert-butyl ester (from Example 37, Step A) (17 mg, 0.025 mmol) in methylene chloride (0.6 mL) and stirred for 18 hr at room temperature. The solvent was removed by rotoevaporation and the crude solid successively co-evaporated with methylene chloride, toluene, and methanol. The crude solid was purified by flash column chromatography on silica gel eluctted with 0–0.5% acetic acid in 5% methanol/methylene chloride to yield N-(3,5-dichlorobenzenesulfonyl)-(L)-prolyl-(L)-4-(2'-(2-methyl-tetrazol-5-yl)phenyl) phenylalanine as a white solid (9 mg, 57% yield).

MS: m/e 629 (M+1). 400 MHz $^1$H NMR (CD$_3$OD): δ 3.16 (m, 1H), 3.30 (s, 3H), 4.23 (m, 1H), 4.65 (m, 1H), 7.05 (d, 2H), 7.27 (d, 2H), 7.60 (m, 3H), 7.72 (m, 1H), 7.80 (d, 3H). 8.17 (d, 1H).

EXAMPLE 88(L-828,629)

N-(3,5-Dichlorobenzenesulfonyl)-(L)-prolyl-(L)-4-(2'-aminocarbonylphenyl)phenylalanine Step A: N-(3,5-Dichlorobenzenesulfonyl)-(L)-prolyl-(L)-4-(2'-carboxyphenyl)phenylalanine.

A solution of tetrabutylammonium permanganate (465 mg, 1.28 mmol) in pyridine (8 mL) was added to a solution of N-(3,5-dichlorobenzenesulfonyl)-(L)-prolyl-(L)-4-(2'-formylphenyl)phenylalanine, tert-butyl ester (from Example 8) (810 mg, 1.28 mmol) in pyridine. The deep purple solution was stirred for 1.5 hr at room temperature and then poured into an ice cold solution of sodium sulfite (7.5 g) in 5N hydrochloric acid to yield a white precipitate. The mixture was extracted with ethyl acetate (3×50 mL). The organic extracts were dried over anhydrous sodium sulfate, filtered and the solvent removed by rotoevaporation to yield a white solid. This solid was purifed by flash column chromatography on silica gel eluted with 5% methanol in methylene chloride to yield N-(3,5-dichlorobenzenesulfonyl)-(L)-prolyl-(L)-4-(2'-carboxyphenyl)phenylalanine, tert-butyl ester (550 mg, 66% yield).

400 MHz $^1$H NMR (CD$_3$OD): δ 1.45 (s, 9H), 3.47 (m, 1H), 4.20 (m, 1H), 4.63 (m, 1H), 7.29 (m, 5H), 7.39 (t, 1H), 7.50 (t, 1H), 7.74 (d, 1H), 7.80 (m, 3H), 8.21 (d, 1H).

Step B: N-(3,5-Dichlorobenzenesulfonyl)-(L)-prolyl-(L)-4-(2'-aminocarbonylphenyl)phenylalanine, tert-butyl ester.

To a solution of N-(3,5-dichlorobenzenesulfonyl)-(L)-prolyl-(L)-4-(2'-carboxyphenyl)phenylalanine, tert-butyl ester (400 mg, 0.618 mmol) in tetrahydrofuran (4 mL) cooled to −5° C. was added N-methylmorpholine (68 μL, 0.618 mmol) and isobutyl chloroformate (80 μL, 0.618 mmol). The solution was stirred for 5 min and then an aqueous solution of 30% ammonium hydroxide (0.10 mL, 0.928 mmol) was added. After stirring for 1 hr at room temperature, the mixture was concentrated by rotoevaporation. The residue was purified by flash column chromatography on silica gel eluted with 2–5% methanol in methylene chloride to yield N-(3,5-dichlorobenzenesulfonyl)-(L)-prolyl-(L)-4-(2'-aminocarbonylphenyl)phenylalanine, tert-butyl ester (110 mg).

Step C: N-(3,5-Dichlorobenzenesulfonyl)-(L)-prolyl-(L)-4-(2'-aminocarbonylphenyl)phenylalanine. (L-828629)

Trifluoroacetic acid (148 μL, 1.92 mmol) was added to a solution of N-(3,5-dichlorobenzenesulfonyl)-(L)-prolyl-(L)-4-(2'-aminocarbonylphenyl)phenylalanine, tert-butyl ester (110 mg, 0.17 mmol) and stirred for 18 hr at room temperature. The reaction was concentrated by rotoevaporation and the solid successively co-evaporated with methylene chloride, toluene and methanol. The residue was purifed by flash column chromatography on silica gel eluted with 0–0.5% acetic acid in 5% methanol/methylene chloride to give N-(3,5-dichlorobenzenesulfonyl)-(L)-prolyl-(L)-4-(2'-aminocarbonylphenyl)phenylalanine as a white solid (14 mg).

MS: m/e 590 (M+1). 400 MHz $^1$H NMR (CD$_3$OD): δ 3.45 (m, 1H), 4.22 (m, 1H), 4.71 (t, 1H), 7.30–7.40 (m, 6H), 7.46 (t, 1H), 7.53 (d, 1H), 7.78 (d, 3H).

The following compounds were also prepared by analogous procedures described in Example 88:

| EXAMPLE NUMBER | | Name | MS* |
|---|---|---|---|
| 828802 | (89) | N-(3,5-dichlorobenzenesulfonyl)-(L)-prolyl-(L)-4-(2'-methylaminocarbonylphenyl)phenylalanine; | 604 (M + 1); 621 (M + NH$_4$ |
| 828803 | (90) | N-(3,5-dichlorobenzenesulfonyl)-(L)-prolyl-(L)-4-(2'-dimethylaminocarbonylphenyl)phenylalanine; | 618 (M + 1), 635 (M + NH$_4$ |
| 829353 | (91) | N-(benzenesulfonyl)-(L)-2(S)-methyl-prolyl-(L)-4-(2'-carboxyphenyl)phenylalanine; | 554 (M + NH$_4$ |
| 835366 | (92) | N-(3-chlorobenzenesulfonyl)-(L)-2(S)-methyl-prolyl-(L)-4-(2'-dimethylaminocarbonylphenyl)phenylalanine; | 615.4 |
| 832630 | (93) | N-(3,5-dichlorobenzenesulfonyl)-(L)-2(S)-methyl-prolyl-(L)-4-(2'-methylaminocarbonylphenyl)phenylalanine; | 604 |
| 832629 | (94) | N-(3,5-dichlorobenzenesulfonyl)-(L)-2(S)-methyl-prolyl-(L)-4-(2'-dimethylaminocarbonylphenyl)phenylalanine; | 632 |

*m/e, (M$^+$) or (M + H$^+$) or (M + NH$_4$$^+$).

EXAMPLE 95 L-828,568

N-(1-Butanesulfonyl)-(L-)-prolyl-(L)-4-(2'-cyanophenyl)phenylalanine

Step A: N-(tert-Butyloxycarbonyl)-(L)-prolyl-(L)-4-iodophenylalanine, tert-butyl ester To a solution of N-(tert-butyloxycarbonyl)-(L)-proline (1.12 g, 5.20 mmol) in methylene chloride (100 mL) were added 1-hydroxybenzotriazole (1.04 g, 7.70 mmol), N-methylmorpholine (1.4 mL, 12.7 mmol), and 4-iodo-(L)-phenylalanine, tert-butyl ester hydrochloride (2.0 g, 5.21 mmol). After cooling in an ice-bath for 5 minutes, 1-(3-dimethylaminopropyl)-3-ethylcarbodiimide hydrochloride (EDC) (1.19 g, 6.21 mmol) was added. After 15 minutes, the cooling bath was removed, and the mixture was stirred overnight under a nitrogen atmosphere. The mixture was diluted with methylene chloride, successively washed with water, 1N hydrochloric acid, saturated sodium bicarbonate solution, and saturated salt solution, and dried over anhydrous magnesium sulfate. The solvent was removed by rotoevaporation and the residue purified by flash column chromatography on silica gel eluted with 25% ethyl acetate in hexane to afford N-(tert-butyloxycarbonyl)-(L)-prolyl-(L)-4-iodophenylalanine, tert-butyl ester (2.37 g, 84% yield).

Step B: N-(tert-Butyloxycarbonyl)-(L)-prolyl-(L)-4-(trimethylstannyl)phenylalanine, tert-butyl ester This intermediate was prepared following the procedure described in Step A of Example 28, using N-(tert-butyloxycarbonyl)-(L)-prolyl-(L)-4-iodophenylalanine, tert-butyl ester as starting material. The compound was obtained pure by flash column chromatography on silica gel eluted with 20% ethyl acetate in hexane (69% yield).

Step C: N-(tert-Butyloxycarbonyl)-(L)-prolyl-(L)-4-(2'-cyanophenyl)phenylalanine, tert-butyl ester This intermediate was prepared following the procedure described in Step B of Example 28, using N-(tert-butyloxycarbonyl)-(L)-prolyl-(L)-4-(trimethylstannyl)phenylalanine, tert-butyl ester as starting material and purified by flash column chromatography in silica gel eluted with 20% ethyl acetate in hexane.

Step D: (L)-Prolyl-(L)-4-(2'-cyanophenyl)phenylalanine tert-butyl ester hydrochloride N-(tert-Butyloxycarbonyl)-(L)-prolyl-(L)-4-(2'-cyanophenyl)phenylalanine, tert-butyl ester (1.11 g, 2.14 mmol) was stirred with 1M hydrochloric acid in ethyl acetate (10.6 mL) overnight at room temperature. The reaction mixture was rotoevaporated and co-evaporated several times with diethyl ether. Flash column chromatography on silica gel eluted with 5% methanol in methylene chloride afforded (L)-Prolyl-(L)-4-(2'-cyanophenyl)phenylalanine, tert-butyl ester hydrochloride (742 mg, 76% yield).

400 MHz $^1$H NMR (CD$_3$OD): δ 1.44 (s, 9H); 3.08 (dd, 1H); 3.18–3.31 (m, 3H); 4.11 (dd, 1H); 4.67 (dd, 1H); 7.39–7.82 (m, 8H).

Step E: N-(1-Butanesulfonyl)-(L-)-prolyl-(L)-4-(2'-cyanophenyl)phenylalanine, tert-butyl ester To a solution of (L)-prolyl-(L)-4-(2'-cyanophenyl) phenylalanine, tert-butyl ester hydrochloride (45 mg, 0.099 mmol) in methylene chloride (2 mL) were added N,N-diisopropylethylamine (52 μL, 0.299 mmol), 4-dimethylaminopyridine (2 mg, 0.016 mmol), and 1-butanesulfonyl chloride (20 μL, 0.154 mmol). The reaction mixture was stirred overnight at room temperature, diluted with methylene chloride, successively washed with water, 2N hydrochloric acid, saturated sodium bicarbonate solution, and saturated salt solution. After drying over anhydrous magnesium sulfate, the solvent was removed by rotoevaporation and the residue purified by flash column chromatography on silica gel eluted with 15–20% acetone in hexane to afford N-(1-butanesulfonyl)-(L-)-prolyl-(L)-4-(2'-cyanophenyl)phenylalanine, tert-butyl ester (24.4 mg, 46% yield).

400 MHz $^1$H NMR (CD$_3$OD): δ 0.92 (t, 3H); 1.45 (s, 9H); 3.01 (dd, 1H); 3.25 (dd, 1H); 4.29 (dd, 1H); 4.67 (dd, 1H); 7.38–7.82 (m, 8H).

Step F: N-(1-Butanesulfonyl)-(L-)-prolyl-(L)-4-(2'-cyanophenyl)phenylalanine

A cooled solution of N-(1-butanesulfonyl)-(L-)-prolyl-(L)-4-(2'-cyanophenyl)phenylalanine, tert-butyl ester (22 mg, 0.041 mmol) in methylene chloride (2.0 mL) was treated with trifluoroacetic acid (0.10 mL, 1.30 mmol). The cooling bath was removed, and the mixture was stirred overnight at room temperature. The reaction mixture was then rotoevaporated, co-evaporated with methylene chloride (3×), toluene (2×), and finally methanol. The residue was purified by flash column chromatography on silica gel eluted with 0–0.1% acetic acid in 3% methanol in methylene chloride to afford N-(1-butanesulfonyl)-(L-)-prolyl-(L)-4-(2'-cyanophenyl)phenylalanine (17 mg).

MS: m/e 484 (M+H); 501 (M+NH$_4$); 400 MHz $^1$H NMR (CD$_3$OD): δ 0.90 (t, 3H); 1.40 (m, 2H); 3.03 (m, 2H); 3.13 (dd, 1H); 4.29 (dd, 1H); 4.77 (m, 1H); 7.38–7.82 (m, 8H).

The following compounds were also prepared by analogous procedures described in Example 95 using the appropriate aryl halide in Step C and the appropriate acyl or sulfonyl halide derivative in Step E:

| EXAMPLE NUMBER | | Name | MS* |
|---|---|---|---|
| 828564 | (96) | N-(3-bromobenzenesulfonyl)-(L)-prolyl-(L)-4-(2'-cyanophenyl)phenylalanine; | 601 |
| 828565 | (97) | N-(benzenesulfonyl)-(L)-prolyl-(L)-4-(2'-cyanophenyl)phenylalanine; | 521 |
| 828567 | (98) | N-(α-toluenesulfonyl)-(L)-prolyl-(L)-4-(2'-cyanophenyl)phenylalanine; | 535 |
| 828569 | (99) | N-(phenylacetyl)-(L)-prolyl-(L)-4-(2'-cyanophenyl)phenylalanine;; | 499 |
| 828570 | (100) | N-(3-pyridinesulfonyl)-(L)-prolyl-(L)-4-(2'-cyanophenyl)phenylalanine; | 505 |
| 829031 | (101) | N-(2-thienylsulfonyl)-(L)-prolyl-(L)-4-(2'-cyanophenyl)phenylalanine; | 527 |
| 829045 | (102) | N-(benzylaminocarbonyl)-(L)-prolyl-(L)-4-(2'-cyanophenyl)phenylalanine; | 497 |
| 829093 | (103) | N-(3-phenylpropionyl)-(L)-prolyl-(L)-4-(2'-cyanophenyl)phenylalanine; | 496 |
| 829136 | (104) | N-((5-methyl-3,4-thiadiazol-2-yl)sulfonyl)-(L)-prolyl-(L)-4-(2'-cyanophenyl)phenylalanine; | 543 |
| 829137 | (105) | N-((benzothiazol-2-yl)sulfonyl)-(L)-prolyl-(L)-4-(2'-cyanophenyl)phenylalanine; | 578 |
| 829355 | (106) | N-((1-methyl-imidazol-4-yl)sulfonyl)-(L)-prolyl-(L)-4-(2'-cyanophenyl)phenylalanine; | 508 |
| 832453 | (107) | N-(3-iodobenzenesulfonyl)-(L)-prolyl-(L)-4-(2'-cyanophenyl)phenylalanine; | 647.0 |
| 832541 | (108) | N-(methanesulfonyl)-(L)-prolyl-(L)-4-(2'-cyanophenyl)phenylalanine; | 459.2 |
| 832789 | (109) | N-(trifluoromethanesulfonyl)-(L)-prolyl-(L)-4-(2'-cyanophenyl)phenylalanine; | 513.3 |
| 835332 | (110) | N-(3-bromobenzenesulfonyl)-(L)-2(S)-methyl- | 613.4 |

-continued

| EXAMPLE NUMBER | | Name | MS* |
|---|---|---|---|
| 835634 | (111) | prolyl-(L)-4-(2'-cyanophenyl)phenylalanine; N-(3,5-dichlorobenzenesulfonyl)-(L)-2(S)-(3-propenyl)-prolyl-(L)-4-(2'-cyanophenyl)phenylalanine; | 629.4 |
| 835728 | (112) | N-(3,5-di(trifluoromethyl)benzenesulfonyl)-(L)-2(S)-methyl-prolyl-(L)-4-(2'-cyanophenyl)phenylalanine; | 671A |
| 837311 | (113) | N-(3,5-dichlorobenzenesulfonyl)-(L)-2(S)-propyl-prolyl-(L)-4-(2'-cyanophenyl)phenylalanine; | 631.3 |
| 837422 | (114) | N-(methanesulfonyl)-(L)-2(S)-methyl-prolyl-(L)-4-(2'-cyanophenyl)phenylalanine; | 473.3 |
| 832666 | (115) | N-(acetyl)-(L)-prolyl-(L)-4-(2'-cyanophenyl)phenylalanine; | 406.4 |
| 844678 | (116) | N-(acetyl)-(L)-2(S)-methyl-prolyl-(L)-4-(2'-cyanophenyl)phenylalanine; | 420.1 |
| 843251 | (117) | N-(3,5-dichlorobenzenesulfonyl)-(L)-2(S)-methyl-pipecolyl-(L)-4-(2'-cyanophenyl)phenylalamine; | 618.4 |
| 837458 | (118) | N-(2-naphthalenesulfonyl)-(L)-2(S)-methyl-prolyl-(L)-4-(2'-cyanophenyl)phenylalanine; | 585.4 |
| 832787 | (119) | N-(methanesulfonyl)-(L)-4(R)-amino-prolyl-(L)-4-(2'-cyanophenyl)phenylalanine; | 458 |
| 832788 | (120) | N-(isopropanesulfonyl)-(L)-4(R)-amino-prolyl-(L)-4-(2'-cyanophenyl)phenylalanine; | 485 |
| 331466 | (121) | N-(t-butanesulfonyl)-(L)-prolyl-(L)-4-(2'-cyanophenyl)phenylalanine; | 501.3 |
| 832992 | (122) | N-(3-trifluoromethylbenzenesulfonyl)-(L)-2(S)-methyl-prolyl-(L)-4-(2'-methoxyphenyl)phenylalanine; | 608 |
| 835241 | (123) | N-(3-chlorobenzenesulfonyl)-(L)-2(S)-methyl-prolyl-(L)-4-(21-methoxyphenyl)phenylalanine; | 574 |

*m/e, (M+) or (M + H+) or (M + NH4+).

EXAMPLE 124 L-835605

N-(3,5-Dichlorobenzenesulfonyl)-(L)-2(S)-methyl-prolyl-(L)-4-(2-pyridyl-N-oxide)phenylalanine Step A: N-(3,5-Dichlorobenzenesulfonyl)-(L)-2(S)-methyl-prolyl-(L)-4-(2-pYridyl-N-oxide)phenylalanine, t-butyl ester.

To a solution of N-(3,5-dichlorobenzenesulfonyl)-(L)-2(S)-methyl-prolyl-(L)-4-(2-pyridyl)phenylalanine, t-butyl ester (from the preparation of Example 65) (21 mg, 0.034 mmol) in methylene chloride (1 mL) was added in portions m-chloroperoxybenzoic acid (50–60%, 24 mg, 0.068 mmol) over a 1 min period. The reaction was stirred at room temperature overnight. The solution was diluted with methylene chloride (50 mL) which was subsequently washed with saturated sodium bicarbonate (2×10 mL) and saturated salt solution (1×10 mL). After drying over anhydrous sodium sulfate, the mixture was filtered and concentrated by rotoevaporation. The residue was purified by flash column chromatography on silica gel eluted with 5% methanol in methylene chloride to yield the title compound (12.6 mg, 58% yield).

MS: m/e=634 (M+H+).

Step B: N-(3,5-Dichlorobenzenesulfonyl)-(L)-2(S)-methyl-prolyl-(L)-4-(2-pyridyl-N-oxide)phenylalanine.

To a solution of N-(3,5-dichlorobenzenesulfonyl)-(L)-2(S)-methyl-prolyl-(L)-4-(2-pyridyl-N-oxide)phenylalanine, t-butyl ester (12.6 mg, 0.02 mmol) in methylene chloride (1 mL) was added trifluoroacetic acid (98 µL). The solution was stirred at room temperature overnight. The solvent was removed by rotoevaporation and residue co-evaporated with fresh methylene chloride (2×) and toluene (4×). The residue was pumped under high vacuum to give the title compound as a solid (13 mg, ~100% yield).

MS: m/e=578 (M+H+).

EXAMPLE 125 L-837421

N-(3,5-Dichlorobenzenesulfonyl)-(L)-2(S)-methyl-prolyl-(L)-4-(3-pyridyl-N-oxide)phenylalanine N-(3,5-Dichlorobenzenesulfonyl)-(L)-2(S)-methyl-prolyl-(L)-4-(3-pyridyl-N-oxide)phenylalanine was prepared by the procedures described in Example 124 from the t-butyl ester of Example 66.

MS: m/e=578 (M+H+).

EXAMPLE 126 829402

N-(3,5-Dichlorobenzenesulfonyl)-(L)-prolyl-(L)-4-(2'-methylsulfinylphenyl)phenylalanine Step A: N-(3,5-Dichlorobenzenesulfonyl)-(L)-prolyl-(L)-4-(2'-methylsulfinylphenyl)phenylalanine, tert-butyl ester.

To a solution of N-(3,5-dichlorobenzenesulfonyl)-(L)-prolyl-(L)-4-(2'-methylthiophenyl)phenylalanine, tert-butyl ester (22 mg, 0.034 mmol) in methylene chloride (1.0 mL) was added 3-chloroperoxybenzoic acid (12 mg, 0.034 mmol). After stirring the solution at room temperature for 15 min, solid sodium bisulfite (25 mg) was added and the solvent removed by rotoevaporation. The remaining solid was purified by flash column chromatography on silica gel eluted with 25% acetone in hexane to afford N-(3,5-dichlorobenzenesulfonyl)-(L)-prolyl-(L)-4-(2'-methylsulfinylphenyl)phenylalanine, tert-butyl ester (15 mg) which was used in the subsequent reaction.

Step B: N-(3,5-Dichlorobenzenesulfonyl)-(L)-prolyl-(L)-4-(2'-methylsulfinylphenyl)phenylalanine.

Trifluoroacetic acid (111 µL) was added to an ice cooled solution of N-(3,5-dichlorobenzenesulfonyl)-(L)-prolyl-(L)-

4-(2'-methylsulfinylphenyl)phenylalanine, tert-butyl ester (15 mg) in methylene chloride (1.0 mL). After stirring for 18 hr at room temperature, the solvent was removed by rotoevaporation to yield N-(3,5-dichlorobenzenesulfonyl)-(L)-prolyl-(L)-4-(2'-methylsulfinylphenyl)phenylalanine (14.6 mg) as a 1:1 mixture of sulfoxide diastereomers.

MS: m/e=609 (M+1). 400 MHz $^1$H NMR (CD$_3$OD): δ 2.43, 2.44 (s, 3H), 3.46 (m, 1H), 4.23 (m, 1H), 4.74 (m, 1H), 7.35 (m, 3H), 7.42 (m, 2H), 7.61 (m, 3H), 7.79 (s, 2H), 8.00 (d, 1H), 8.32 (d, 1H).

EXAMPLE 127 829403

N-(3,5-Dichlorobenzenesulfonyl)-(L)-prolyl-(L)-4-(2'-methylsulfonylphenyl)phenylalanine Step A: N-(3,5-Dichlorobenzenesulfonyl)-(L)-prolyl-(L)-4-(2'-methylsulfonylphenyl)phenylalanine, tert-butyl ester.

To a solution of N-(3,5-dichlorobenzenesulfonyl)-(L)-prolyl-(L)-4-(2'-methylthiophenyl)phenylalanine, tert-butyl ester (22 mg, 0.034 mmol) in methylene chloride (1.0 mL) was added 3-chloroperoxybenzoic acid (24 mg, 0.068 mmol) in two equal portions 15 min apart. After stirring the solution at room temperature for 4 hr, solid sodium bisulfite (25 mg) was added and the solvent removed by rotoevaporation. The remaining solid was purified by flash column chromatography on silica gel eluted with 25% acetone in hexane to afford N-(3,5-dichlorobenzenesulfonyl)-(L)-prolyl-(L)-4-( 2'-methylsulfonylphenyl)phenylalanine, tert-butyl ester (15 mg) which was used in the subsequent reaction.

Step B: N-(3,5-Dichlorobenzenesulfonyl)-(L)-prolyl-(L)-4-(2'-methylsulfonylphenyl)phenylalanine.

Trifluoroacetic acid (111 μL) was added to an ice cooled solution of N-(3,5-dichlorobenzenesulfonyl)-(L)-prolyl-(L)-4-(2'-methylsulfonylphenyl)phenylalanine, tert-butyl ester (15 mg) in methylene chloride (1.0 mL). After stirring for 18 hr at room temperature, the solvent was removed by rotoevaporation to yield N-(3,5-dichlorobenzenesulfonyl)-(L)-prolyl-(L)-4-(2'-methylsulfonylphenyl)phenylalanine (14.3 mg).

MS: m/e=624 (M), 642 (M+NH4). 400 MHz $^1$H NMR (CD$_3$OD): δ 2.65, 2.44 (s, 3H), 3.50 (m, 1H), 4.22 (m, 1H), 4.75 (m, 1H), 7.39 (m, 3H), 7.48 (t, 1H), 7.61 (m, 1H), 7.69 (t, 1H), 7.81 (d, 3H), 7.97 (m, 1H), 8.15 (d, 1H), 8.28 (d, 1H).

The following compounds were also prepared by analogous procedures described in Example 127:

| EXAMPLE NUMBER | | Name | MS* |
|---|---|---|---|
| 835244 | (128) | N-(3-chlorobenzenesulfonyl)-(L)-2(S)-methyl-prolyl-(L)-4-(2'-methylsulfonylphenyl)phenylalanine | 622.3 |
| 832842 | (129) | N-(3,5-dichlorobenzenesulfonyl)-(L)-2(S)-methyl-prolyl-(L)-4-(2'-methylsulfonylphenyl)phenylalanine | 639 |

*m/e, (M$^+$) or (M + H$^+$) or (M + NH$_4^+$).

EXAMPLE 130 L-333169

N-(3,5-Dichlorobenzenesulfonyl)-(L)-2(S)-methyl-prolyl-(L)-4-(3-methyl-1,2,4-oxadiazol-5-yl)-phenylalanine Step A: N-Boc-(L)-4-iodophenylalanine, t-butyl ester.

To a solution of 15 g (51 mmol) of (L)-4-iodophenylalanine in 100 ml of diglyme and 15 ml of conc. H$_2$SO$_4$ was added 30 ml of condensed isobutylene. The vessel was agitated overnight and the crude product was diluted with 100 ml of ethyl acetate. The solution was added to excess sodium hydroxide solution while maintaining the temperature below 30° C. A white precipitate formed which dissolved upon addition of sodium hydroxide solution. The resulting mixture was filtered and the aqueous phase was extracted with ethyl acetate. The combined extracts were washed with brine and dried over anhydrous magnesium sulfate. The mixture was filtered and concentrated in vacuo to give a solution of the product in diglyme. The solution was diluted with 200 ml of ether and was treated with excess 1N HCl in ether with rapid stirring. The resulting precipitate was collected and dried in vacuo after washing with ether. A white solid (9.01 g) was collected. To a suspension of 7.5 g (19 mmol) of the amine hydrochloride in 100 ml of methylene chloride was added 2.52 g (19 mmol) of diisopropyl ethyl amine followed by 4.14 g (0.019 g) of di t-butyl dicarbonate. The solution was stirred overnight at room temperature, washed with 1N HCl solution (2×50 ml), water (1×50 ml), saturated sodium carbonate solution (1×50 ml) and brine (1×50 ml). The solution was dried over MgSO$_4$, filtered and concentrated in vacuo to give 8.8 g of N-Boc-(L)-4-iodophenylalanine, t-butyl ester as an oil.

300 MHz $^1$H NMR (CDCl$_3$): δ 1.4 (s, 18H); 2.98 (m, 2H); 4.40 (dd, 1H); 4.98 (d, 1H); 6.90 (d, 2H), 7.60 (d, 2H).

Step B: N-Boc-L-4-(3-methyl-1,2,4-oxadiazol-5-yl)-phenylalanine, t-butyl ester.

To a solution of 0.32 g (0.71 mmol) of N-Boc-(L)-4-iodophenylalanine, t-butyl ester in 3.0 ml of toluene contained in a 5 ml round bottom flash fitted with a condenser topped with a T-valve (one side of which is connected to a balloon of carbon monoxide the other side to a vacuum source) was added 0.15 g (2.1 mmol) of methyl amide oxime, 25 mg of bistriphenylphosphine palladium dichloride and 0.14 g (1.4 mmol) of triethylamine. The vessel was evacuated and flushed with CO gas three times and then heated at 90° C. under CO overnight. The reaction mixture was diluted with 25 ml of ethyl acetate and washed with water (2×25 ml) and brine (1×25 ml). The mixture was filtered and concentrated in vacuo. The residue was purified by Biotage flash chromatography eluted with 15% ethyl acetate/hexanes to give 0.18 g of the desired product (63% yield). 300 MHz $^1$H NMR (CDCl$_3$): δ 1.40 (s, 18H); 2.42 (s, 3H); 3.10 (m, 2H); 4.45 (dd, 1H); 5.09 (d, 1H); 7.31 (d, 2H); 8.0 (d, 2H).

Step C: Boc-N-(L)-α-methyl-prolyl-(L)-4-(3-methyl-1,2,4-oxadiazol-5-yl)-phenylalanine, t-butyl ester.

N-Boc-L-4-(3-methyl-1,2,4-oxadiazol-5-yl)-phenylalanine t-butyl ester (0.18 g, 0.46 mmol) was stirred overnight with 5 equivalents of 1.5M HCl/ethyl acetate solution. The resulting white precipitate was filtered and dried in vacuo to give 0.12 g (0.35 mmol) of the amine hydrochloride. The amine hydrochloride was suspended in 1.5 ml of methylene chloride and treated with 0.089 g (0.4 mmol) N-Boc-α-methylproline, 0.2 g (0.4 mmol) PyBOP and 0.15 g (1.17 mmol) of diisopropylethylamine. The mixture was stirred over night at room temperature, diluted with 25 ml of methylene chloride and washed with water and brine and dried over $MgSO_4$. The mixture was filtered and concentrated in vacuo. The residue was purified by Biotage flash chromatography eluting with 25% ethyl acetate/hexanes to give 0.1 g of the title product (55% yield) which was used in the subsequent reaction.

300 MHz $^1$H NMR ($CDCl_3$): δ 1.39 (s, 18H); 1.40–1.70 (m, 4H); 2.41 (s, 2H); 3.09 and 3.19 (dAB, 2H); 3.40 (bd, 2H); 4.68 (dd, 1H); 7.40 (d, 2H); 7.98 (d, 2H).

Step D: N-(3,5-Dichlorobenzenesulfonyl)-(L)-2(S)-methyl-prolyl-(L)-4-(3-methyl-1,2,4-oxadiazol-5-yl)-phenylalanine, t-butyl ester.

The product of Step C was stirred over night with 5 equivalents of 1.5M HCl/Ethyl acetate solution in 0.5 ml of additional ethyl acetate. The resulting white precipitate was concentrated in vacuo and was used directly in the next step. The material was suspended in 1.5 ml of methylene chloride and was treated with 52 mg (0.21 mmol) 3,5-dichlorophenylsulfonylchloride, 25 mg of dimethylaminopyridine and 60 mg (0.46 mmol) of diisopropylethylamine. After 2 hours an additional amount of 3,5-dichlorophenylsulfonylchloride (25 mg) and diisopropylethylamine (60 mg) was added. The mixture was stirred over 48 hours, diluted with ethyl acetate and washed with 1N HCl, saturated sodium bicarbonate solution and brine and was dried over anhydrous $MgSO_4$. The mixture was filtered and concentrated in vacuo. The residue was purified by Biotage flash chromatography eluting with 30% ethyl acetate/hexanes to give 0.039 g of the title compound (55% yield).

300 MHz 1H NMR ($CDCl_3$): δ 1.45 (s, 9H); 1.65 (s, 3H); 1.4–1.8 (m, 4H); 3.19 and 3.30 (dAB, 2H); 3.30 (m, 1H); 3.49 (m, 1H); 4.75 (q, 1H); 7.12 d, 1H); 7.39 (d, 2H); 7.52 (s,1H); 7.75 (s, 2H); 8.02 (d, 2H).

Step E: N-(3,5-Dichlorobenzenesulfonyl)-(L)-2(S)-methyl-prolyl-(L)-4-(3-methyl-1,2,4-oxadiazol-5-yl)-phenylalanine.

N-(3,5-Dichlorobenzenesulfonyl)-(L)-2(S)-methyl-prolyl-(L)-4-(3-methyl-1,2,4-oxadiazol-5-yl)-phenylalanine, t-butyl ester (39 mg) was stirred for 2 hours with 2 ml of 50% methylene chloride/trifluoroacetic acid and concentrated in vacuo. The residue was purified by preparatory thin layer chromatography over silica eluting with 10% methanol/methylene chloride/1% acetic acid to give 27.1 mg of the title compound.

FABMS:calc for C24H24Cl2N4O6S1=566; obs:567 ($M^+$+1).). 300 MHz $^1$H NMR ($CD_3OD$): δ 1.59 (s, 3H); 1.70–1.85 (m, 4H); 2.41 (s, 3H); 3.20 (dd, 1H); 3.35–3.45 (m, 3H); 4.75 (dd, 1H); 7.49 (d, 2H); 7.67 (s,1HO; 7.72 (5, 2H); 8.02 (d, 2H).

EXAMPLE 131

N-(3,5-Dichlorobenzenesulfonyl)-(L)-prolyl-(L)-4-(3-methyl-1,2,4-oxadiazol-5-yl)-phenylalanine The compound was prepared as described in Example 130 but utilizing N-(3,5-dichlorophenylsulfonyl)-(L)-proline in place of N-Boc-α-methylproline in Step C and coupling in the presence of HBTU, HOBt and diisopropylethylamine. The product of this reaction (purified by Biotage flash chromatography eluting with 30% Ethyl acetate/hexanes) was submitted to Step E to give the desired product.

FABMS:calc for C23H22Cl2N4O6S1=552; obs:553 ($M^+$+1).

EXAMPLE 132 L-832267

N-(Benzenesulfonyl)-(L)-prolyl-2(S)-amino-3(R)-(4-(2'-cyano)biphenl)-butyric acid Step A 2(S)-amino-3(R)-(4-iodophenyl)-butric acid.

Following a literature procedure (J. Org. Chem. 59, 4206 (1994)), to a solution of 2(S)-amino-3(R)-phenyl-butyric acid (100 mg, 0.46 mmol) (which was prepared by the procedures described by Hruby et al. (Tetrahedron 48, 4733 (1992))) in acetic acid (0.4 mL) containing sulfuric acid (0.055 mL), iodine (47 mg, 0.18 mmol) and sodium iodate (19 mg, 0.10 mmol) was added and the solution heated to 70° C. for 21 hr. Fresh aliquots of iodine (47 mg) and sodium iodate (19 mg) were added and the reaction continued to be heated for 15 hr. The solvents were removed by rotoevaporation and the residue was purifed on a Biotage flash column chromatography apparatus using a C18 column eluted with 2:1 methanol:water to yield the title compound.

Step B 2(S)-Amino-3(R)-(4-iodophenyl)-butyric acid, methyl ester hydrochloride.

To an ice cooled solution of 2(S)-amino-3(R)-(4-iodophenyl)-butyric acid (124 mg, 0.42 mmol) in methanol (0.5 mL) was added dropwise thionyl chloride (150 μL, 2.0 mmol). Methanol (1 mL) was added and the reaction mixture was heated to reflux for 2 hr. After cooling, the mixture was filtered and the filtrate concentrated by rotoevaporation to yield 2(S)-amino-3(R)-(4-iodophenyl)-butyric acid, methyl ester hydrochloride (116 mg, 82% yield).

Step C: N-(Benzenesulfonyl)-(L)-prolyl-2(S)-amino-3(R)-(4-iodophenyl)-butyric acid, methyl ester.

To an ice cooled solution of 2(S)-amino-3(R)-(4-iodophenyl)-butyric acid, methyl ester hydrochloride (116 mg, 0.34 mmol), N-(benzenesulfonyl)-(L)-proline (128 mg, 0.50 mmol), HOBt (77 mg, 0.5 mmol) and N-methylmorpholine (55 μL, 0.5 mmol) was added 1-(3-dimethylaminopropyl)-3-ethylcarbodiimide hydrochloride (EDC, 99 mg, 0.5 mmol). After stirring overnight, the solvents were removed by rotoevaporation, and the residue was dissolved in methylene chloride and loaded onto a flash silica gel chromatography column. The product was eluted with 10% ethyl acetate in methylene chloride to yield 163 mg (85% yield) of the title compound.

Steps D–F N-(Benzenesulfonyl)-(L)-prolyl-2(S)-amino-3 (R)-(4-(2'-cyano)biphenyl)-butyric acid.

Employing the procedures described in Example 3, Steps D and E, N-(benzenesulfonyl)-(L)-prolyl-2(S)-amino-3(R)-(4-iodophenyl)-butyric acid, methyl ester was converted to N-(benzenesulfonyl)-(L)-prolyl-2(S)-amino-3(R)-(4-(2'-cyano)biphenyl)-butyric acid, methyl ester. The methyl ester was hydrolyzed in the presence of sodium hydroxide in methanol according to Example 3, Step C to yield N-(benzenesulfonyl)-(L)-prolyl-2(S)-amino-3(R)-(4-(2'-cyano)biphenyl)-butyric acid.

MS: m/e=535 ($M+NH_4^+$).

EXAMPLE 133 L-832268

N-(Benzenesulfonyl)-(L)-prolyl-2(S)-amino-3(S)-(4-(2'-cyano)biphenyl)-butyric acid The title compound was prepared according to the procedures described in Example 132 but substituting 2(S)-amino-3(S)-phenyl-butyric acid in Step A.

MS: m/e=535 (M+NH$_4^+$).

EXAMPLE 134 L-835627

N-(Benzenesulfonyl)-(L)-4(R)-N-(N',N'-dimethylformamidino)-prolyl-(L)-4-(2'-cyanophenyl)phenylalanine To a solution of N-(benzenesulfonyl)-(L)-4(R)-aminoprolyl-(L)-4-(2'-cyanophenyl)phenylalanine (from Example 37) (17 mg, 0.03 mmol) in dry methanol (0.3 mL) was added dimethylformamide dimethylacetal (4 µL, 0.03 mmol). The reaction was stirred at room temperature for 2 hr and filtered through a pad of C18 silica gel eluted with water to 50% methanol in water. The solvents were removed by rotoevaporation and the residue purified by preparative thin layer chromatography on reverse phase C18 plates eluted with 50% acetonitrile in water. The UV active band was combined with a drop of trifluroacetic acid and filtered through a PrepSep-C18 pad washed with methanol. The filtrate was concentrated to dryness to yield N-(benzenesulfonyl)-(L)-4(R)-N-(N',N'-dimethylformamidino)-prolyl-(L)-4-(2'-cyanophenyl)phenylalanine.

MS: m/e=574 (M+H$^+$).

EXAMPLE 135 L-835628

N-(Benzenesulfonyl)-(L)-4(R)-dimethylamino-prolyl-(L)-4-(2'-cyanophenyl)phenylalanine To a suspension of N-(benzenesulfonyl)-(L)-4(R)-aminoprolyl-(L)-4-(2'-cyanophenyl)phenylalanine (from Example 37) (19 mg, 0.037 mmol) in acetonitrile (0.2 mL) was added 37% formaldehyde (14 µL, 0.18 mmol) followed by the addition of sodium cyanoborohydride (3.8 mg, 0.06 mmol). After stirring for 5 min, fresh quantities of 37% formaldehyde (10 µL) and sodium cyanoborohydride (3 mg) were added and the reaction stirred overnight. The reaction was diluted with acetonitrile (2 mL) and quenched with acetic acid (0.5 mL and water (4 mL). The solvents were removed by rotoevaporation and the residue loaded onto a C18 PrepSep Extract column. The column was washed with water (5 mL) then a gradient of methanol/water. The filtrate was concentrated and the residue purified on preparative reverse phase C18 plates eluted with 1:1 acetonitrile/water. The UV active band was removed with methanol, filtered, dissolved in methanol containing a drop of trifluoroacetic acid and passed through a PrepSep C18 pad prewashed with methanol and eluted with methanol to yield the the title compound.

MS: m/e=547 (M+H$^+$).

EXAMPLE 136

Inhibition of VLA-4 Dependent Adhesion to BSA-CS-1 Conjugate

Step A. Preparation of CS-1 Coated Plates.

Untreated 96 well polystyrene flat bottom plates were coated with bovine serum albumin (BSA; 20 µg/ml) for 2 hours at room temperature and washed twice with phosphate buffered saline (PBS). The albumin coating was next derivatized with 10 µg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 µg/ml and allowed to react for 2 hours at room temperature. The plates were washed twice with PBS and stored at 4° C.

Step B. Preparation of Fluorescently Labeled Jurkat Cells.

Jurkat cells, clone E6-1, obtained from the American Type Culture Collection (Rockville, Md.; cat #ATCC TIB-152) were grown and maintained in RPMI-1640 culture medium containing 10% fetal calf serum (FCS), 50 units/ml penicillin, 50 µg/ml streptomycin and 2 mM glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of 2×10$^6$ cells/ml in PBS containing a 1 µM concentration of a fluorogenic esterase substrate (2', 7'-bis-(2-carboxyethyl)-5-(and -6)-carboxyfluorescein, acetoxymethyl ester; BCECF-AM; Molecular Probes Inc., Eugene, Oreg.; catalog #B-1150) for 30–60 minutes at 37° C. in a 5% CO$_2$/air incubator. The fluorescently labeled Jurkat cells were washed two times in PBS and resuspended in RPMI containing 0.25% BSA at a final concentration of 2.0×10$^6$ cells/ml.

Step C. Assay Procedure.

Compounds of this invention were prepared in DMSO at 100× the desired final assay concentration. Final concentrations were selected from a range between 0.001 nM–100 µM. Three µL of diluted compound, or vehicle alone, were premixed with 300 µL of cell suspension in 96-well polystyrene plates with round bottom wells. 100 µL aliquots of the cell /compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the IC$_{50}$ was determined from a ten point titration using a validated four parameter fit algorithm.

EXAMPLE 137

Antagonism of VLA-4 Dependent Binding to
VCAM-Ig Fusion Protein

Step A. Preparation of VCAM-Ig.

The signal peptide as well as domains 1 and 2 of human VCAM (GenBank Accession no. M30257) were amplified by PCR using the human VCAM cDNA (R & D Systems) as template and the following primer sequences:
3'-PCR primer:
  5'-AATTATAATTTGATCAACTTACCTGTCAAT TCTTTTACAGCCTGCC-3';
5'-PCR primer:
  5'-ATAGGAATTCCAGCTGCCACCATGCCT GGGAAGATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:
MPGKMVVILGASNILWIMFAASQAFKI-ETTPESRYLAQIGDSVSLTC STTGCESPFFSWRTQ IDSPLNGKVTNEGTTSTLTMNPVSFGNEHSYLC TAT-CESRKLEKGIQVEIYSFPKDPEIHLSG-PLEAGKPITVKCSVADVY PFDRLEIDLLKGDHLMK-SQEFLEDADRKSLETKSLEVTFTPVIEDIGKV LVCRAKLHIDEMDSVPTVRQAVKEL.

The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 µg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B. Preparation of $^{125}$I-VCAM-Ig.

VCAM-Ig was labeled to a specific radioactivity greater that 1000 Ci/mmole with $^{125}$I-Bolton Hunter reagent (New England Nuclear, Boston, Mass.; cat #NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C. VCAM-Ig Binding Assay.

Compounds of this invention were prepared in DMSO at 100× the desired final assay concentration. Final concentrations were selected from a range between 0.001 nM–100 µM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with MnCl$_2$ at a final concentration of 1 mM. Compounds were assayed in Millipore MHVB multiscreen plates (cat#MHVBN4550, Millipore Corp., Mass.) by making the following additions to duplicate wells: (i) 200 µL of binding buffer containing 1 mM MnCl$_2$; (ii) 20 µL of $^{125}$I-VCAM-Ig in binding buffer containing 1 mM MnCl$_2$ (final assay concentration ~100 µM); (iii) 2.5 µL of compound solution or DMSO; (iv) and 0.5×10$^6$ cells in a volume of 30 µL. The plates were incubated at room temperature for 30 minutes, filtered on a vacuum box, and washed on the same apparatus by the addition of 100 µL of binding buffer containing 1 mM MnCl$_2$. After insertion of the multiscreen plates into adapter plates (Packard, Meriden, Conn., cat#6005178), 100 µL of Microscint-20 (Packard cat#6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Contol wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the IC$_{50}$ was determined from a ten point titration using a validated four parameter fit algorithm.

EXAMPLE 138

Antagonism of $\alpha_4\beta_7$ Dependent Binding to VCAM-Ig Fusion Protein

Step A. $\alpha_4\beta_7$ Cell Line.

RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 U penicillin/100 µg streptomycin/2 mM L-glutamine at 37° C., 5% carbon dioxide. The cells were pelleted at 1000 rpm for 5 minutes and then washed twice and resuspended in binding buffer (25 mM Hepes, 150 mM NaCl, 0.1% BSA, 3 mM KCl, 2 mM Glucose, pH 7.4).

Step B. VCAM-Ig Binding Assay.

Compounds of this invention were prepared in DMSO at 100× the desired final assay concentration. Final concentrations were selected from a range between 0.001 nM–100 µM. Compounds were assayed in Millipore MHVB multiscreen plates (Cat#MHVBN4550) by making the following sequential additions to duplicate wells: (i) 100 μl/well of binding buffer containing 1.5 mM $MnCl_2$; (ii) 10 μl/well $^{125}$I-VCAM-Ig in binding buffer (final assay concentration<500 μM); (iii) 1.5 μl/well test compound or DMSO alone; (iv) 38 μl/well RPMI-8866 cell suspension (1.25×10$^6$ cells/well). The plates were incubated at room temperature for 45 minutes on a plate shaker at 200 rpm, filtered on a vacuum box, and washed on the same apparatus by the addition of 100 μL of binding buffer containing 1 mM $MnCl_2$. After insertion of the multiscreen plates into adapter plates (Packard, Meriden, Conn., cat#6005178), 100 μL of Microscint-20 (Packard cat#6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the $IC_{50}$ was determined from a ten point titration using a validated four parameter fit algorithm.

What is claimed is:

1. A compound having the formula Ia:

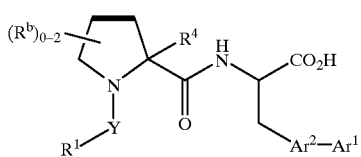

Ia wherein
$R^1$ is
1) $C_{1-10}$alkyl,
2) Cy, or
3) Cy—$C_{1-10}$alkyl,
wherein alkyl is optionally substituted with one to four substituents independently selected from $R^a$; and Cy is optionally substituted with one to four substituents independently selected from $R^b$; $R^4$ is
1) hydrogen, or
2) $C_{1-3}$alkyl;
$Ar^1$ and $Ar^2$ are independently aryl or heteroaryl each of which is optionally substituted with one to four substituents independently selected from $R^b$;
$R^a$ is
1) Cy
2) —$OR^d$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N-OR^e)$,
22) $CF_3$; or
23) —$OCF_3$;
wherein Cy is optionally subsituted with one to four substituents independently selected from $R^c$;
$R^b$ is
1) a group selected from $R^a$,
2) $C_{1-10}$alkyl,
3) $C_{1-10}$alkenyl,
4) $C_{2-10}$alkynyl,
5) aryl $C_{1-10}$alkyl,
6) heteroaryl $C_{1-10}$alkyl,
wherein alkyl, alkenyl, alkynyl, aryl, heteroaryl are optionally substituted with a group independently selected from $R^c$;
$R^c$ is
1) halogen,
2) amino,
3) carboxy,
4) $C_{1-4}$alkyl,
5) $C_{1-4}$alkoxy,
6) aryl,
7) aryl $C_{1-4}$alkyl,
8) hydroxy,
9) $CF_3$, or
10) aryloxy;
$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^i$
1) $C_{1-10}$alkyl,
2) $C_{2-10}$alkenyl,
3) $C_{2-10}$alkynyl, or
4) aryl;
wherein alkyl, alkenyl, alkynyl and aryl are each optionally substituted with one to four substituents independently selected from $R^c$;

Cy is cycloalkyl, heterocyclyl, aryl, or heteroaryl;
m is an integer from 1 to 2;
n is an integer from 1 to 10; and
Y is $SO_2$.

2. A compound of claim 1 wherein $R^1$ is $C_{1-10}$alkyl, aryl, aryl-$C_{1-10}$alkyl, heteroaryl or heteroaryl-$C_{1-10}$alkyl, wherein alkyl is optionally substituted with one to four substituents independently selected from $R^a$; aryl and heteroaryl are optionally substituted with one to four substituents independently selected from $R^b$.

3. A compound of claim 1 wherein $Ar^1$–$Ar^2$ is 4-($Ar^1$)-phenyl in which $Ar^1$ is optionally substituted with 1 or 2 groups independently selected from $R^b$.

4. A compound of claim 3 wherein $R^b$ is selected from the group consisting of halogen, cyano, trifluoromethyl, trifluoromethoxy, $C_{1-3}$alkyl, $C_{1-3}$alkoxy, $C_{1-3}$alkylthio, 4-(2-hyrdoxymethylphenyl)phenylmethyl, $C(O)R^d$, $C(O)OR^d$, $C(O)NR^dR^e$, $NR^dR^e$, $NR^dC(O)R^e$.

5. A compound of claim 1 wherein $R^1$ is phenyl optionally substituted with one to three groups selected from $R^b$.

6. A compound of claim 3 wherein $Ar^1$ is phenyl optionally substituted with 1 or 2 groups independently selected from halogen, cyano, trifluoromethyl, trifluoromethoxy, $C_{1-3}$alkyl, $C_{1-3}$alkoxy, $C_{1-3}$alkylthio, 4-(2-hydroxymethylphenyl)phenylmethyl, $C(O)R^d$, $C(O)OR^d$, $C(O)NR^dR^e$, $NR^dR^e$, $NR^dC(O)R^e$.

7. A compound of claim 1 wherein $R^1$ is selected from the group consisting of: phenyl, 2-naphthyl, 3,4-dimethoxyphenyl, 3,5-dichlorophenyl, 3,5-di(trifluoromethyl)phenyl, 3-fluorophenyl, 3-chlorophenyl, 3-bromophenyl, 3-iodophenyl, 3-trifluoromethylphenyl, benzyl, methyl, trifluoromethyl, isopropyl, butyl, 3-pyridyl, 2-thienyl, 5-methyl-3,4-thiadiazol-2-yl, 2-benzothiazolyl, and 1-methyl-4-imidazolyl.

8. A compound selected from the group consisting of:

N-(3,5-dichlorobenzenesulfonyl)-(L)-prolyl-(L)-4-biphenylalanine;

N-(3,5-Dichlorobenzenesulfonyl)-(L)-prolyl-(L)-4-(4-fluorophenyl)phenylalanine;

N-(3,5-Dichlorobenzenesulfonyl)-(L-)-prolyl-(L)-4-(2'-thienyl)-phenylalanine;

N-(3,5-Dichlorobenzenesulfonyl)-(L-)-prolyl-(L)-4-(3'-thienyl)-phenylalanine;

N-(3,5-Dichlorobenzenesulfonyl)-(L-)-prolyl-(L)-4-(4'-trifluoromethyl-penyl)-phenylalanine;

N-(3,5-Dichlorobenzenesulfonyl)-(L-)-prolyl-(L)-4-(2'-methoxy-phenyl)-phenylalanine;

N-(3,5-Dichlorobenzenesulfonyl)-(L)-prolyl-(L)-4-(2'-formyl-phenyl)-phenylalanine;

N-(3-fluorobenzenesulfonyl)-(L)-prolyl-(L)-4-(3'-thienyl)phenylalanine;

N-(3,5-dichlorobenzenesulfonyl)-(L)-prolyl-(L)-4-(2',6'-difluorophenyl)phenylalanine;

N-(3,5-dichlorobenzenesulfonyl)-(L)-prolyl-(L)-4-(2'-hydroxymethylphenyl)phenylalanine;

N-(3,5-dichlorobenzenesulfonyl)-(L)-prolyl-(L)-4-(4'-methylphenyl)phenylalanine;

N-(3,5-dichlorobenzenesulfonyl)-(L)-prolyl-(L)-4-(2'-carboxyphenyl)phenylalanine;

N-(3,5-dichlorobenzenesulfonyl)-(L)-prolyl-(L)-4-(2'-methoxyearbonyl)phenylalanine;

N-(3,5-dichlorobenzenesulfonyl)-(L)-prolyl-(L)-4-(3'-foamylphenyl)phenylalanine;

N-(3,5-dichlorobenzenesulfonyl)-(L)-prolyl-(L)-4-(3'-aminophenyl)phenylalanine;

N-(3,5-dichlorobenzenesulfonyl)-(L)-prolyl-(L)-4-(2'-metliylphenyl)phenylalanine;

N-(3,5-dichlorobenzenesulfonyl)-(L)-prolyl-(L)-4-(3'-acetamidophenyl)phenylalanine;

N-(3,5-dichlorobenzenesulfonyl)-(L)-prolyl-(L)-4-(2'-fluorophenyl)phenylalanine;

N-(3,5-dichlorobenzenesulfonyl)-(L)-prolyl-(L)-4-(3'-carboxyphenylphenyl)phenylalanine;

N-(3,5-dichlorobenzenesulfonyl)-(L)-prolyl-(L)-4-(3'-methoxycarbonylphenyl)phenylalanine;

N-(3,5-dichlorobenzenesulfonyl)-(L)-prolyl-(L)-4-(2',4'-dichlorophenyl)phenylalanine;

N-(3,5-dichlorobenzenesulfonyl)-(L)-prolyl-(L)-4-(2'-formyl-3-thienyl)phenylalanine;

N-(3,5-dichlorobenzenesulfonyl)-(L)-2(S)-methyl-prolyl-(L)-4-(4'-fluorophenyl)phenylalanine;

N-(3,5-dichlorobenzenesulfonyl)-(L)-2(S)-methyl-prolyl-(L)-4-(2'-formylphenyl)phenylalanine;

N-(3,5-dichlorobenzenesulfonyl)-(L)-2(S)-methyl-prolyl-(L)-4-(2'-(hydroxymethyl)phenyl)-phenylalanine;

N-(3,5-dichlorobenzenesulfonyl)-(L)-2(S)-methyl-prolyl-(L)-4-(2'-cyanophenyl)phenylalanine;

N-(benzenesulfonyl)-(L)-2(S)-methyl-prolyl-(L)-4-(2'-formylphenyl)phenylalanine;

N-(benzenesulfonyl)-(L)-2(S)-methyl-prolyl-(L)-4-(2'-methoxyphenyl)phenylalanine;

N-(3-chlorobenzenesulfonyl)-(L)-2(S)-methyl-prolyl-(L)-4-(2'-methylthiophenyl)phenylalanine;

N-(3,5-dichlorobenzenesulfonyl)-(L)-2(S)-methyl-prolyl-(L)-4-(2'-methoxyphenyl)-2-thienylalanine;

N-(3,5-dichlorobenzenesulfonyl)-(D)-2(R)-methyl-prolyl-(D)-4-(2'-cyanophenyl)phenylalanine;

N-(3,5-dichlorobenzenesulfonyl)-(D)-2(R)-methyl-prolyl-(L)-4-(2'-cyanophenyl)phenylalanine;

N-(3,5-dichlorobenzenesulfonyl)-(L)-2(S)-methyl-prolyl-(L)-4-(2'-methoxyphenyl)phenylalanine;

N-(3,5-dichlorobenzenesulfonyl)-(L)-2(S)-methyl-prolyl-(L)-4-(2'-methylthiophenyl)phenylalanine;

N-(3,5-dichlorobenzenesulfonyl)-(L)-3(R)-methyl-prolyl-(L)-4-(2'-methoxyphenyl)-phenylalanine, methyl ester;

N-(benzenesulfonyl)-(L)-4(R)-amino-prolyl-(L)-4-(2'-cyanophenyl)phenylalanine;

N-(benzenesulfonyl)-(L)-4(S)-amino-prolyl-(L)-4-(2'-cyanophenyl)phenylalanine;

N-(3,5-dichlorobenzenesulfonyl)-(L)-2(S)-methyl-prolyl-(L)-4-(2'-trifluoromethoxyphenyl)phenylalanine;

N-(benzenesulfonyl)-(L)-4(R)-benzoylamino-prolyl-(L)-4-(2'-cyanophenyl)phenylalanine;

N-(benzenesulfonyl)-(L)-4(S)-benzoylamino-prolyl-(L)-4-(2'-cyanophenyl)phenylalanine;

N-(benzenesulfonyl)-(L)-4(R)-phenylacetylamino-prolyl-(L)-4-(2'-cyanophenyl)phenylalanine;

N-(benzenesulfonyl)-(L)-4(S)-phenylacetylamino-prolyl-(L)-4-(2'-cyanophenyl)phenylalanine;

N-(3,5-Dichlorobenzenesulfonyl)-(L)-prolyl-(L)-N-methyl-4-(2'-methoxyphenyl)phenylalanine;

N-(3,5-Dichlorobenzenesulfonyl)-(L)-3(S)-methyl-prolyl-(L)-N-methyl-4-(2'-methoxyphenyl)phenylalanine;

N-(3-fluorobenzenesulfonyl)-(L)-prolyl-(L)-4-(2'-cyanophenyl)phenylalanine;

N-(3,5-dichlorobenzenesulfonyl)-(L)-proly-(L)-4-(4'-fluoro-2'-methoxyphenyl)phenylalanine;

N-(3,5-dichlorobenzenesulfonyl)-(L)-prolyl-(L)-4-(2'-cyanophenyl)phenylalanine;

N-(3,5-dichlorobenzenesulfonyl)-(L)-prolyl-(L)-4-(2'-methylthiophenyl)phenylalanine;

N-(3,5-dichlorobenzenesulfonyl)-(L)-prolyl-(L)-4-(2'-(5-methyl-1,3,4-oxadiazol-2-yl-phenyl)phenylalanine;

N-(3,5-dichlorobenzenesulfonyl)-(L)-prolyl-(L)-4-(2-methyl-5-trifluoromethyl-benzoxazol-7-yl)phenylalanine;

N-(3,5-dichlorobenzenesulfonyl)-(L)-prolyl-(L)-4-(2-methyl-6-(5-trifluoromethyl-tetrazol-1-yl)-benzoxazol-4-yl)phenylalanine;

N-(3,5-dichlorobenzenesulfonyl)-(L)-prolyl-(L)-4-(2-methyl-5-(5-tri fluoromethyl-tetrazol-1-yl)-benzoxazol-7-yl)phenylalanine;

N-(3,5-dichlorobenzenesulfonyl)-(L)-prolyl-(L)-4-(3-pyridyl)phenylalanine;

N-(3,5-dichlorobenzenesulfonyl)-(L)-prolyl-(L)-4-(2-pyridyl)phenylalanine;

N-(3,5-dichlorobenzenesulfonyl)-(L)-prolyl-(L)-4-(5-pyrimidinyl)phenylalanine;

N-(3,5-dichlorobenzenesulfonyl)-(L)-prolyl-(L)-4-(3'-cyanophenyl)phenylalanine;

N-(3,5-dichlorobenzenesulfonyl)-(L)-prolyl-(L)-4-(2-methyl-benzoxazol-4-yl)phenylalanine;

N-(3,5-dichlorobenzenesulfonyl)-(L)-prolyl-(L)-4-(6-acetamido-2-methyl-benzoxazol-4-yl)-phenylalanine;

N-(benzenesulfonyl)-(L)-prolyl-(L)-4-(2-pyridyl)phenylalanine;

N-(3,5-dichlorobenzenesulfonyl)-(L)-3(S)-methylprolyl-(L)-4-(2'-cyanophenyl)phenylalanine;

N-(benzenesulfonyl)-(L)-2(S)-methyl-prolyl-(L)-4-(2'-cyanophenyl)phenylalanine;

N-(3-chlorobenzenesulfonyl)-(L)-2(S)-methyl-prolyl-(L)-4-(2'-cyanophenyl)phenylalanine;

N-(3-chlorobenzenesulfonyl)-(L)-2(S)-methyl-prolyl-(L)-4-(5-pyrimidinyl)phenylalanine;

N-(3-trifluoromethylbenzenesulfonyl)-(L)-2(S)-methyl-prolyl-(L)-4-(2'-cyanophenyl)phenylalanine;

N-(3,5-dichlorobenzenesulfonyl)-(L)-2(S)-methyl-prolyl-(L)-4-(3-pyridyl)phenylalanine;

N-(3,5-dichlorobenzenesulfonyl)-(L)-2(S)-methyl-prolyl-(L)-4-(5-pyrimidinyl)phenylalanine;

N-(3,5-dichlorobenzenesulfonyl)-(L)-2(S)-methyl-prolyl-(L)-4-(3'-cyano-phenyl)phenylalanine;

N-(3,5-dichlorobenzenesulfonyl)-(L)-2(S)-methyl-prolyl-(L)-4-(5'-fluoro-2'-methoxy-phenyl)phenylalanine;

N-(3,5-dichlorobenzenesulfonyl)-(L)-2(S)-methyl-proyl-(L)-4-(2'-methoxy-5'-trifluoromethyl-phenyl)phenylalanine;

N-(3,5-dichlorobenzenesulfonyl)-(L)-2(S)-methyl-prolyl-(L)-4-(2-pyridyl)phenylalanine;

N-(3,5-dichlorobenzenesulfonyl)-(L)-2(S)-methyl-prolyl-(L)-4-(3'-fluoro-2'-cyanophenyl)phenylalanine;

N-(3,5-dichlorobenzenesulfonyl)-(L)-2(S)-methyl-prolyl-(L)-4-(2'-trifluoromethylsulfonyl-phenyl)phenylalanine;

N-(3,5-dichlorobenzenesulfonyl)-(L)-2(S)-methyl-prolyl-(L)-4-(2-thiazolyl)phenylalanine;

N-(3,5-dichlorobenzenesulfonyl)-(L)-2(S)-methyl-prolyl-(L)-4-(5-(1H,3H-pyrimidine-2,4-dione)-phenylalanine;

N-(3,5-dichlorobenzenesulfonyl)-(L)-2(S)-methyl-prolyl-(L)-4-(4'-fluoro-3'-cyano-phenyl)-phenylalanine;

N-(3,5-dichlorobenzenesulfonyl)-(L)-2(S)-methyl-prolyl-(L)-4-(2'-fluoro-5'-cyano-phenyl)phenylalanine;

N-(3,5-dichlorobenzenesulfonyl)-(L)-2(S)-methyl-prolyl-(L)-4-(1-methyl-7-indolyl)-phenylalanine;

N-(3,5-dichlorobenzenesulfonyl)-(L)-2(S)-methyl-prolyl-(L)-4-(7-indolyl)phenylalanine;

N-(3,5-dichlorobenzenesulfony)-(L)-2(S)-methyl-prolyl-(L)-4-(4-benzthi azolyl)phenylalanine;

N-(3,5-dichlorobenzenesulfonyl)-(L)-2(S)-methyl-prolyl-(L)-4-(4-benzoxazolyl)phenylalanine;

N-(3,5-Dichlorobenzenesulfonyl)-(L)-2(S)-methyl-prolyl-(L)-4-(2-methyl-4-benzoxazolyl)-phenylalanine;

N-(3,5-Dichlorobenzenesulfonyl)-(L)-2(S)-methyl-prolyl-(L)-4-(2-trifluoromethyl-4-benzoxazolyl)phenylalanine;

N-(3,5-dichlorobenzenesulfonyl)-(L)-2(S)-methyl-prolyl-(L)-4-(2'-isopropyloxy-phenyl)-phenylalanine;

N-(3,5-Dichlorobenzenesulfonyl)-(L)-prolyl-(L)-4-(2'-(tetrazol-5-yl)phenyl)phenylalanine;

N-(3,5-Dichlorobenzenesulfonyl)-(L)-prolyl-(L)-4-(2'-(2-methyl-tetrazol-5-yl)phenyl)-phenylalanine;

N-(3,5-Dichlorobenzenesulfonyl)-(L)-prolyl-(L)-4-(2'-(3-methyl-tetrazol-5-yl)phenyl)-phenylalanine;

N-(3,5-Dichlorobenznesulfonyl)-(L)-prolyl-(L)-4-(2'-aminocarbonylphenyl)phenylalanine;

N-(3,5-dichlorobenzenesulfonyl)-(L)-prolyl-(L)-4-(2'-methylaminocarbonylphenyl)-phenylalanine;

N-(3,5-dichlorobenzenesulfonyl)-(L)-prolyl-(L)-4-(2'-dimethylaminocarbonylphenyl)-phenylalanine;

N-(benzenesulfonyl)-(L)-2(S)-methyl-prolyl-(L)-4-(2'-carboxyphenyl)phenylalanine;

N-(3-chlorobenzenesulfonyl)-(L)-2(S)-methyl-prolyl-(L)-4-(2'-dimethylaminocarbonylphenyl)-phenylalanine;

N-(3,5-dichlorobenzenesulfonyl)-(L)-2(S)-methyl-prolyl-(L)-4-(2'-methylaminocarbonylphenyl)phenylalanine;

N-(3,5-dichlorobenzenesulfonyl)-(L)-2(S)-metlyl-prolyl-(L)-4-(2'-dimcthylaminocarbonylphenyl)phenylalanine;

N-(1-Butanesulfonyl)-(L-)-prolyl-(L)-4-(2'-cyanophenyl)phenylalanine;

N-(3-bromobenzenesulfonyl)-(L)-prolyl-(L)-4-(2'-cyanophenyl)phenylalanine;

N-(benzenesulfonyl)-(L)-prolyl-(L)-4-(2'-cyanophenyl)phenylalanine;

N-(a-toluenesulfonyl)-(L)-prolyl-(L)-4-(2'-cyanophenyl)phenylalanine;

N-(3-pyridinesulfonyl)-(L)-prolyl-(L)-4-(2'-cyanophenyl)phenylalanine;

N-(2-thienylsulfonyl)-(L)-prolyl-(L)-4-(2'-cyanophenyl)phenylalanine;

N-5-methyl-3,4-thiadiazol-2-yl)sulfonyl)-(L)-prolyl-(L)-4-(2'-cyanophenyl)phenylalanine;

N-((benzothiazol-2-yl)sulfonyl)-(L)-prolyl-(L)-4-(2'-cyanophenyl)phenylalanine;

N-((1-methyl-imidazol-4-yl)sulfonyl)-(L)-prolyl-(L)-4-(2'-cyanophenyl)phenylalanine;

N-(3-iodobenzenesulfonyl)-(L)-prolyl-(L)-4-(2'-cyanophenyl)phenylalanine;

N-(methanesulfonyl)-(L)-prolyl-(L)-4-(2'-cyanophenyl)phenylalanine;

N-(trifluoromethanesulfonyl)-(L)-prolyl-(L)-4-(2'-cyanophenyl)phenylalanine;

N-(3-bromobenzenesulfonyl)-(L)-2(S)-methyl-prolyl-(L)-4-(2'-cyanophenyl)phenylalanine;

N-(3,5-dichlorobenzenesulfonyl)-(L)-2(S)-(3-propenyl)-prolyl-(L)-4-(2'-cyanophenyl)phenylalanine;

N-(3,5-di(trifluoromethyl)benzenesulfonyl)-(L)-2(S)-methyl-prolyl-(L)-4-(2'-cyanophenyl)phenylalanine;

N-(3,5-dichlorobenzenesulfonyl)-(L)-2(S)-propyl-prolyl-(L)-4-(2'-cyanophenyl)phenylalanine;

N-(methanesulfonyl)-(L)-2(S)-methyl-prolyl-(L)-4-(2'-cyanophenyl)phenylalanine;

N-(2-naphthalenesulfonyl)-(L)-2(S)-methyl-prolyl-(L)-4-(2'-cyanophenyl)phenylalanine;

N-(methanesulfonyl)-(L)-4(R)-amino-prolyl-(L)-4-(2'-cyanophenyl)phenylalanine;

N-(isopropanesulfonyl)-(L)-4(R)-amino-prolyl-(L)-4-(2'-cyanophenyl)phenylalanine;

N-(t-butanesulfonyl)-(L)-prolyl-(L)-4-(2'-cyanophenyl)phenylalanine;

N-(3-trifluoromethylbenzenesulfonyl)-(L)-2(S)-methyl-prolyl-(L)-4-(2'-methoxyphenyl)phenylalanine;

N-(3-chlorobenzenesulfonyl)-(L)-2(S)-methyl-prolyl-(L)-4-(2'-methoxyphenyl)phenylalanine;

N-(3,5-Dichlorobenzenesulfonyl)-(L)-2(S)-methyl-prolyl-(L)-4-(2-pyridyl-N-oxide)-phenylalanine;

N-N-(3,5-Dichlorobenzenesulfonyl)-(L)-2(S)-methyl-prolyl-(L)-4-(3-pyridyl-N-oxide)phenylalanine;

N-(3,5-Dichlorobenzenesulfonyl)-(L)-prolyl-(L)-4-(2'-methylsulfinylphenyl)phenylalanine;

N-(3,5-Dichlorobenzenesulfonyl)-(L)-prolyl-(L)-4-(2'-methylsulfonylphenyl)phenylalanine;

N-(3-chlorobenzenesulfonyl)-(L)-2(S)-methyl-prolyl-(L)-4-(2'-methylsulfonylphenyl)phenylalanine;

N-(3,5-dichlorobenzenesulfonyl)-(L)-2(S)-methyl-prolyl-(L)-4-(2'-methylsulfonylphenyl)phenylalanine;

N-(3,5-Dichlorobenzenesulfonyl)-(L)-2(S)-methyl-prolyl-(L)-4-(3-methyl-1,2,4-oxadiazol-5-yl)phenylalanine;

N-(3,5-Dichlorobenzenesulfonyl)-(L)-prolyl-(L)-4-(3-methyl-1,2,4-oxadiazol-5-yl)phenylalanine;

N-(benzenesulfonyl)-(L)-4(R)-N-(N',N'-dimethylformamidino)-prolyl-(1)-4-(2'-cyanophenyl)phenylalanine; and N-(benzenesulfonyl)-(L)-4(R)-dimethylamino-prolyl-(L)-4-(2'-cyanophenyl)phenylalanine.

9. A method for the treatment of diseases, disorders, conditions or symptoms mediated by cell adhesion in a mammal which comprises administering to said mammal an effective amount of a compound of claim 1.

10. A method for the treatment of asthma, allergic rhinitis, multiple sclerosis, atherosclerosis, inflammatory bowel disease or inflammation in a mammal which comprises administering to said mammal an effective amount of a compound of claim 1.

11. A pharmaceutical composition which comprises a compound of claim 1 and a pharmaceutically acceptable carrier thereof.

* * * * *